(12) United States Patent
Novikov et al.

(10) Patent No.: US 10,360,472 B2
(45) Date of Patent: Jul. 23, 2019

(54) SYSTEM, METHOD AND COMPUTER-ACCESSIBLE MEDIUM FOR DETERMINING BRAIN MICROSTRUCTURE PARAMETERS FROM DIFFUSION MAGNETIC RESONANCE IMAGING SIGNAL'S ROTATIONAL INVARIANTS

(71) Applicants: New York University, New York, NY (US); Albert-Ludwigs-Universität Freiburg, Freiburg (DE)

(72) Inventors: Dmitry Novikov, New York, NY (US); Ileana Jelescu, Lausanne (CH); Jelle Veraart, Brooklyn, NY (US); Els Fieremans, New York, NY (US); Valerij Kiselev, Freiburg (DE); Marco Reisert, Freiburg (DE)

(73) Assignees: New York University, New York, NY (US); Albert-Ludwigs-Universität Freiburg, Freiburg (DE)

( * ) Notice: Subject to any disclaimer, the term of this patent is extended or adjusted under 35 U.S.C. 154(b) by 51 days.

(21) Appl. No.: 15/156,250

(22) Filed: May 16, 2016

(65) Prior Publication Data
US 2016/0343129 A1 Nov. 24, 2016

Related U.S. Application Data

(60) Provisional application No. 62/162,391, filed on May 15, 2015.

(51) Int. Cl.
*G06K 9/00* (2006.01)
*G06K 9/52* (2006.01)
(Continued)

(52) U.S. Cl.
CPC ............... *G06K 9/52* (2013.01); *A61B 5/055* (2013.01); *G01R 33/5608* (2013.01);
(Continued)

(58) Field of Classification Search
None
See application file for complete search history.

(56) References Cited

U.S. PATENT DOCUMENTS

| 5,969,524 A | * | 10/1999 | Pierpaoli | .......... | G01R 33/56341 |
| | | | | | 324/307 |
| 6,992,484 B2 | * | 1/2006 | Frank | ............... | G01R 33/56341 |
| | | | | | 324/307 |

(Continued)

FOREIGN PATENT DOCUMENTS

WO 2014165849 A1 10/2014

OTHER PUBLICATIONS

Alexander, "Multiple-Fiber Reconstruction Algorithms for Diffusion MRI", Department of Computer Science, University College London, London WC1E 6BT, United Kingdom, Ann. N.Y. Acad. Sci. 1064: 113-133 (2005). © 2005 New York Academy of Sciences doi: 10.1196/annals.1340.018, 2005.*

(Continued)

*Primary Examiner* — Shervin K Nakhjavan
(74) *Attorney, Agent, or Firm* — Hunton Andrews Kurth LLP

(57) ABSTRACT

An exemplary system, method and computer-accessible medium for determining a plurality of tissue parameters of a tissue(s), can include, for example, receiving information related to a plurality of rotational invariants contained within a diffusion magnetic resonance (dMR) image(s) of the tissue(s), and generating the tissue parameters using a set of rotational invariants related to the plurality of tissue parameters using such information. The tissue parameters can be generated by factorizing a response of an individual fiber segment of the tissue(s) based on the set of rotational invariants. The response of the individual fiber segments can be factorized from an orientational distribution function ("ODF"). The individual fiber segments can be factorized (Continued)

using a scalar tensor factorization(s) of the rotational invariants. The set of rotational invariants can be of a rotation group SO(3).

29 Claims, 18 Drawing Sheets

(51) Int. Cl.
    *A61B 5/055*     (2006.01)
    *G01R 33/56*     (2006.01)
    *A61B 5/00*     (2006.01)
    *G01R 33/563*     (2006.01)

(52) U.S. Cl.
    CPC .......... *A61B 5/0042* (2013.01); *A61B 5/7203* (2013.01); *A61B 2576/026* (2013.01); *G01R 33/56341* (2013.01)

(56) References Cited

U.S. PATENT DOCUMENTS

| | | | | |
|---|---|---|---|---|
| 2007/0167732 A1* | 7/2007 | Zwanger | .......... | G01R 33/56341 600/410 |
| 2011/0038521 A1* | 2/2011 | Degani | ............ | G01R 33/56341 382/131 |
| 2011/0282183 A1* | 11/2011 | Song | ....................... | A61B 5/055 600/410 |
| 2012/0197105 A1* | 8/2012 | Mezer | ..................... | A61B 5/055 600/410 |
| 2012/0259199 A1* | 10/2012 | Huwer | ............. | G01R 33/56341 600/410 |
| 2015/0130458 A1* | 5/2015 | Topgaard | ............... | G01N 24/08 324/309 |

OTHER PUBLICATIONS

Ghosh, "High Order Models in Diffusion MRI and Applications", PHD thesis, Graduate school of University of Nice-Sophia Antiplis, Nov. 28, 2011.*
Carlo Pierpaoli et al ("Diffusion Tensor MR Imaging of the Human Brain", Radiology, Dec. 1996) (Year: 1996).*
T E J Behrens, et al., "Characterization and propagation of uncertainty in diffusion-weighted MR imaging," Magn Reson Med 50, 1077-88 (2003).
Christopher D Kroenke, et al., "On the nature of the NAA diffusion attenuated MR signal in the central nervous system," Magn Reson Med 52, 1052-9 (2004).
Sune N. Jespersen, et al., "Modeling dendrite density from magnetic resonance diffusion measurements," Neuroimage 34, 1473-1486 (2007).
Sune N. Jespersen, et al., "Neurite density from magnetic resonance diffusion measurements at ultrahigh field: Comparison..." Nieurairnage 49, 205-216 (2010).
Y Assaf, R Z , et al., "New modeling and experimental framework to characterize hindered and restricted water diffusion in brain white matter," MRM, 52, 965-978 (2004).
Els Fieremans, et al., "Monte Carlo study of a two-compartment exchange model of diffusion," NMR in Biomedicine 23, 711-724 (2010).
Els Fieremans, et al., "White matter characterization with diffusional kurtosis imaging," Neuroimage 58, 177-88 (2011).
Hui Zhang, et al. "NODDI: practical in vivo neurite orientation dispersion and density imaging of the human brain," Neuroimage 61, 1000-16 (2012).
Dmitry S Novikov, et al., "Revealing mesoscopic structural universality with diffusion," Proc Natl Acad Sci U S A 111, 5088-93 (2014).
Els Fieremans, et al., "In vivo observation and biophysical interpretation of time-dependent diffusion in human white matter," NeuroImage (2016).
Els Fieremans, et al., "Diffusion distinguishes between axonal loss and demyelination in brain white matter," Proc of the Int'l Society of Magn Reson in Med 20, p. 714 (2012).
Lauren M Burcaw, et al., "Mesoscopic structure of neuronal tracts from time-dependent diffusion," NeuroImage 114, 18-37 (2015).
Dmitry S. Novikov and Els Fieremans, "Relating extracellular diffusivity..." Proc of the Int'l Society of Magn Reson in Med 20, p. 1829 (2012).
Maira Tariq, et al., "Bingham—noddi: Mapping anisotropic orientation dispersion of neurites using diffusion mri," NeuroImage (2016).
Ileana O Jelescu, et al., "Degeneracy in model parameter estimation for multi-compartmental diffusion in neuronal tissue," NMR in Biomedicine 29, 33-47 (2016).
Jens H Jensen, et al., "Fiber ball imaging," NeuroImage 124, 824-833 (2016).
Enrico Kaden, et al., "Quantitative mapping of the per axon diffusion coefficients in brain white matter," Magnetic resonance in medicine (2015).
Jens H Jensen, et al., "Diffusional kurtosis imaging: . . ." Magn Reson Med 53, 1432-40 (2005).
Bibek Dhital, et al., "Isotropic diffusion weighting . . ." Proc of the Int'l Society of Magn Reson in Med 23, p. 2788. (2015).
Filip Szczepankiewicz, et al., "Quantification of microscopic diffusion anisotropy . . . applications in healthy volunteers and in brain tumors," NeuroImage 104, 241-252 (2015).
Marco Reisert, et al., "Mesoft: unifying diffusion modelling and fiber tracking," in Medical image Computing and Computer-Assisted Intervention—MICCAI 2014 (Springer, 2014).
Jelle Veraart, et al., Stefan Sunaert, arid Jan Sijbers, "Comprehensive framework for accurate diffusion mri parameter estimation," Magn Reson Med 70, 972 84 (2013).
Kip S Thorne, "Multipole expansions of gravitational radiation," Reviews of Modern Physics 52, 299 339 (1980).
Stephen M Smith, et al., "Advances in functional and structural MR image analysis and implementation as FSL," Neuroimage 23, S208 S219 (2004).
Jelle Vereart, et al., "Diffusion MRI noise mapping using random matrix theory," Magnetic resonance in medicine DOI: 10.1002/mrm.26059 (2016).
Cheng Guan Koay and Peter J Basser, "Analytically exact correction scheme for signal extraction from noisy magnitude MR signals," Jour. of Magnetic Reson. 179, 317-322 (2006).
Elias Kellner, et al., "Gibbs-ringing artifact removal based on local subvoxel-shifts," Magnetic resonance in medicine DOI: 10.1002/mrm.26054 (2015).
Jelle Veraart, et al., "Gibbs ringing in diffusion MRI," Magnetic resonance in medicine DOI: 10.1002/mrm.25866 (2015).
U.S. Appl. No. 62/162,164, dated May 15, 2015, New York University.

* cited by examiner

Figure 2A
Figure 2B
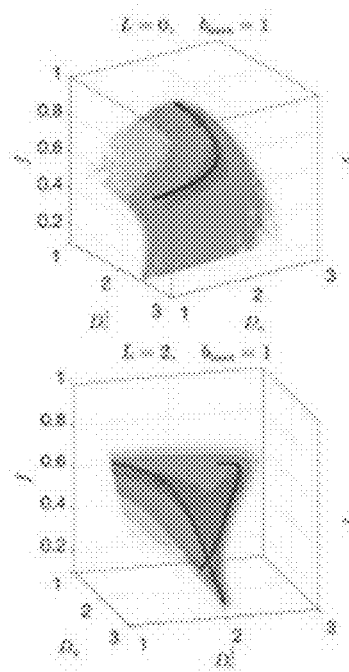
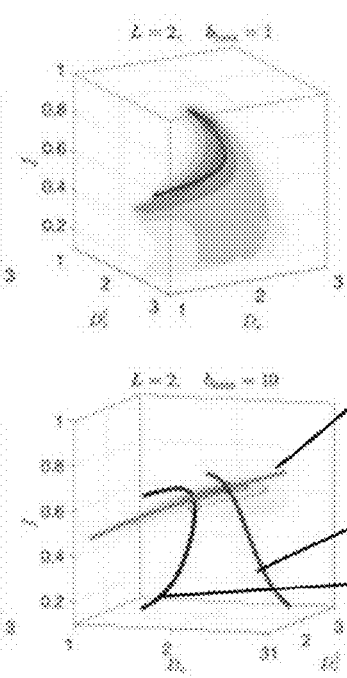
Figure 2C
Figure 2D

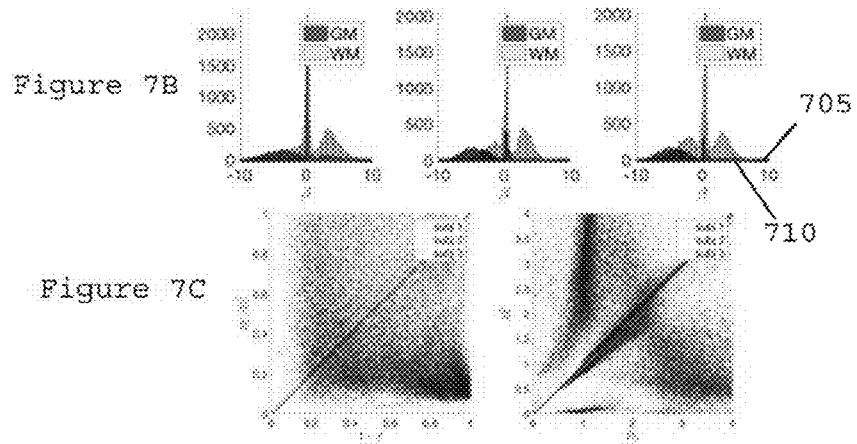

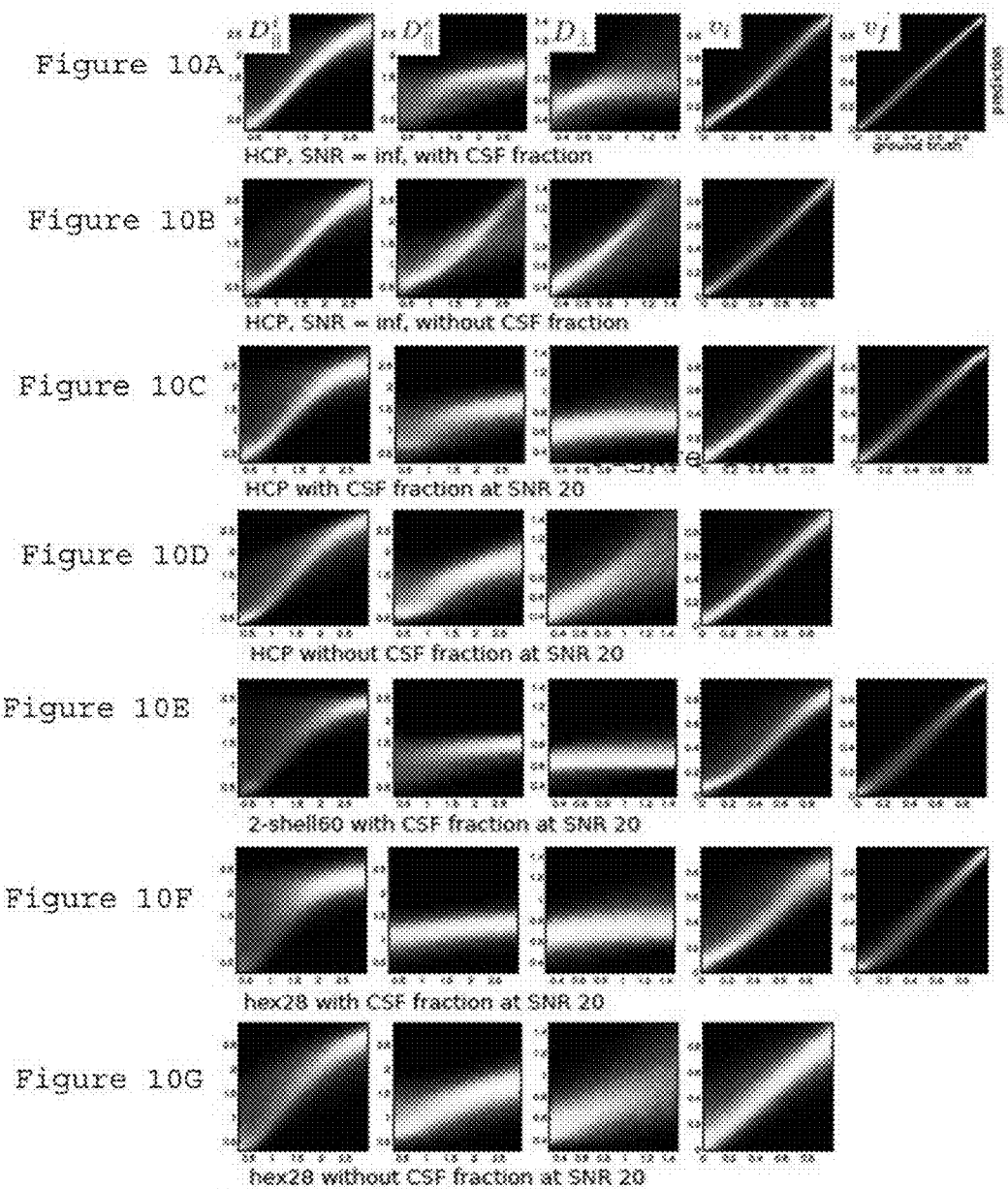

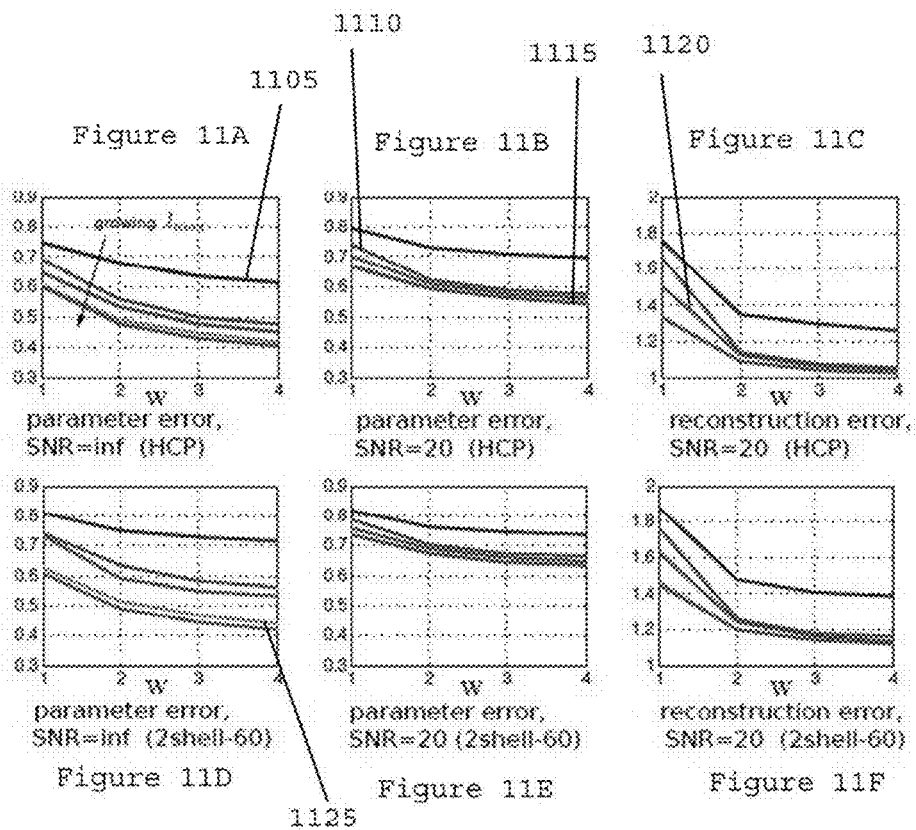

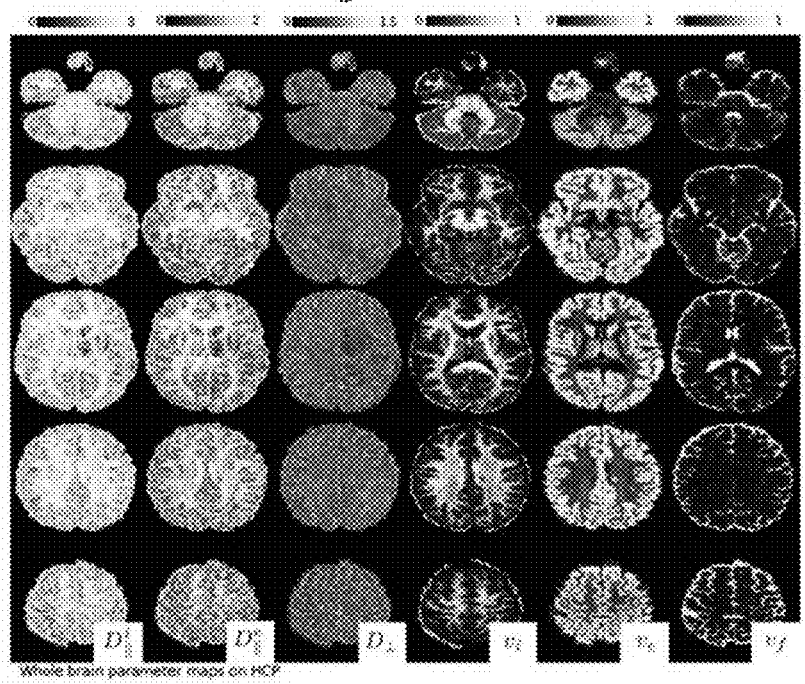
Figure 12A
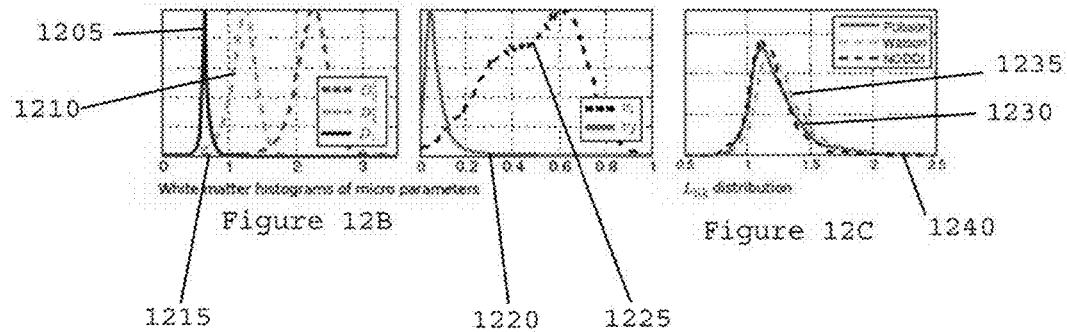
Figure 12B
Figure 12C

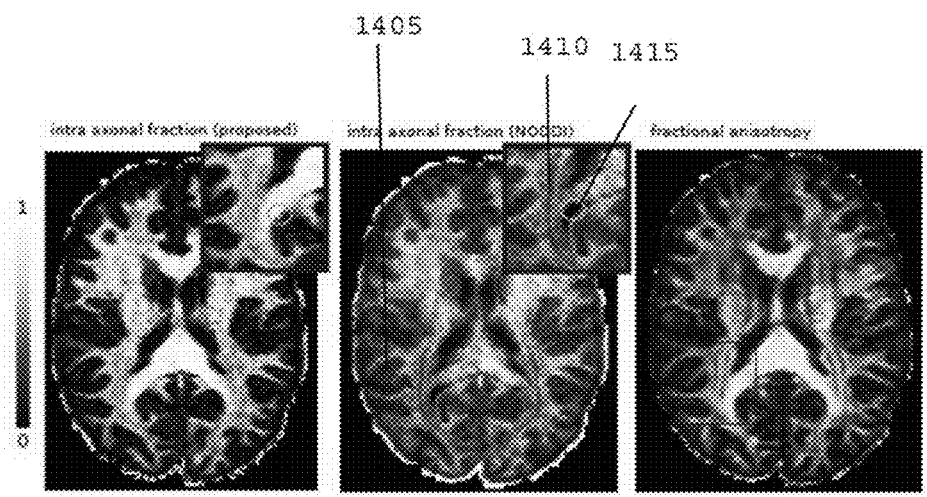
Figure 14A
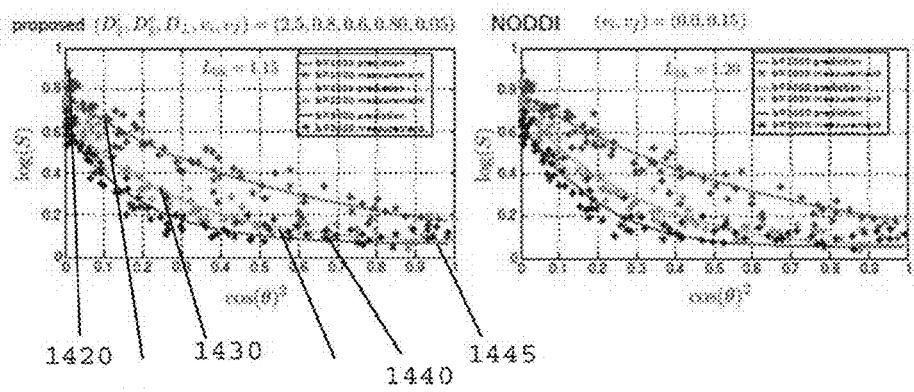
Figure 14B
Figure 14C

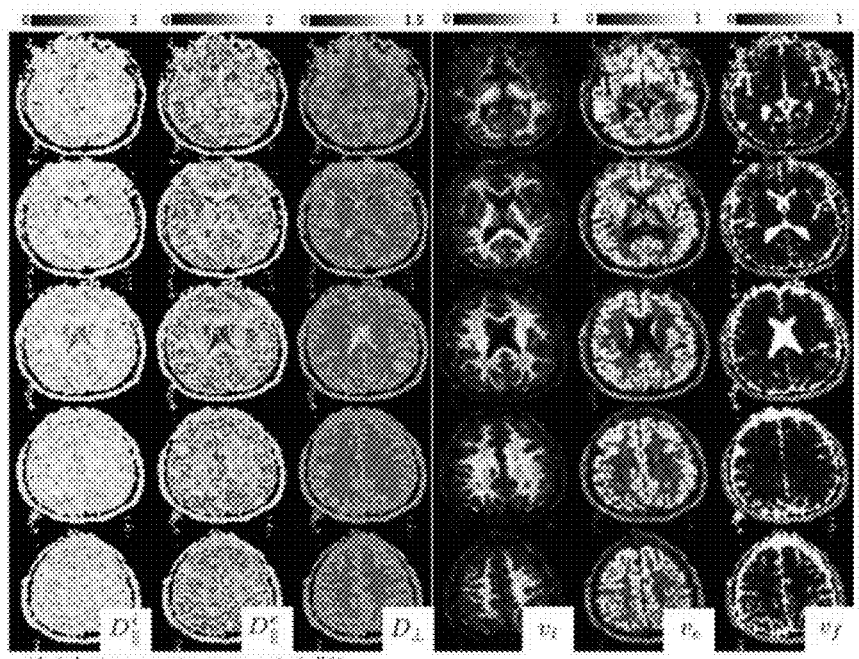
Figure 15A
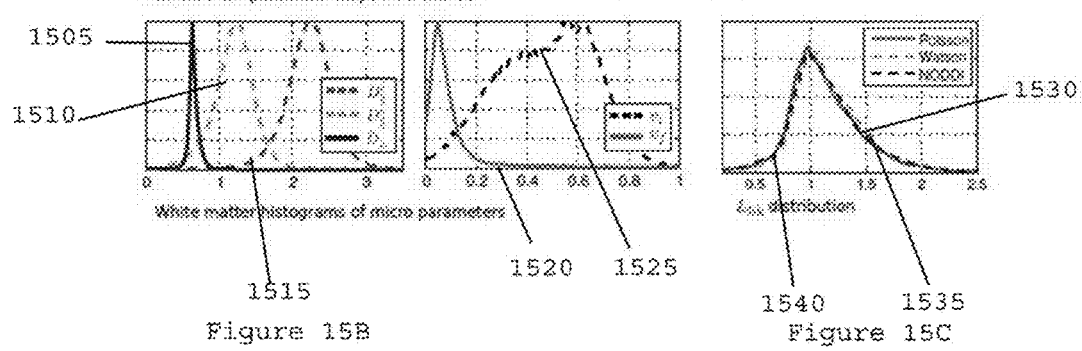
Figure 15B
Figure 15C

Figure 16A
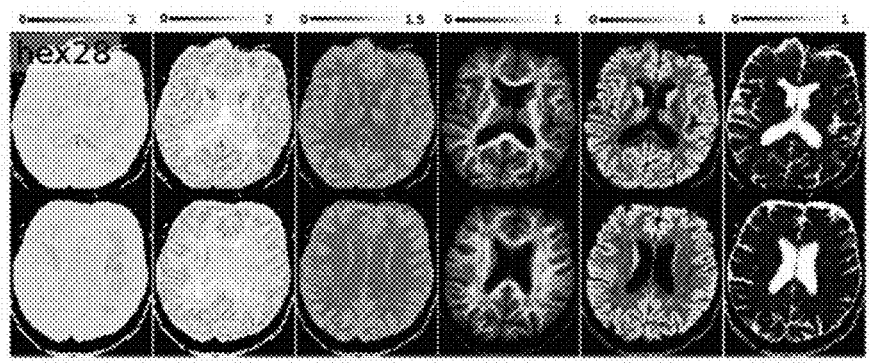
Whole brain parameter maps on hex28
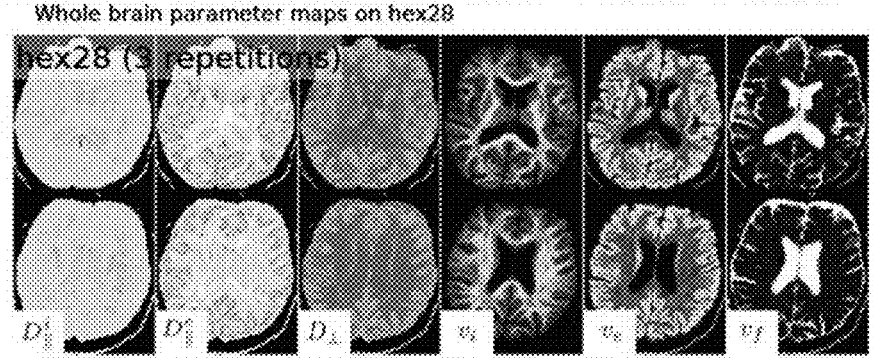
Whole brain parameter maps on hex28 with 3 repetitions
Figure 16B
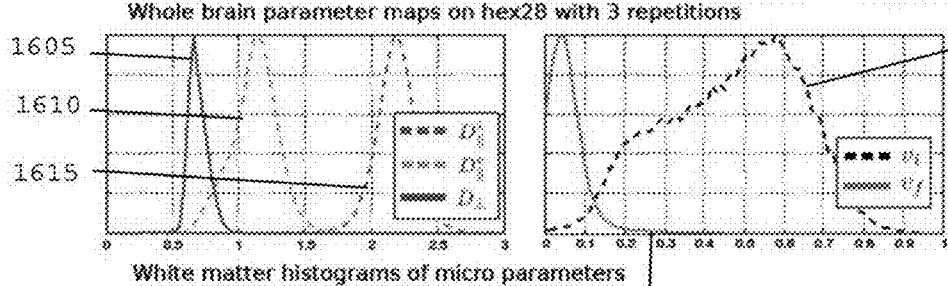
White matter histograms of micro parameters
Figure 16C

SYSTEM, METHOD AND COMPUTER-ACCESSIBLE MEDIUM FOR DETERMINING BRAIN MICROSTRUCTURE PARAMETERS FROM DIFFUSION MAGNETIC RESONANCE IMAGING SIGNAL'S ROTATIONAL INVARIANTS

CROSS-REFERENCE TO RELATED APPLICATION(S)

This application relates to and claims priority from U.S. Patent Application No. 62/162,391, filed on May 15, 2015, the entire disclosure of which is incorporated herein by reference.

STATEMENT REGARDING FEDERALLY SPONSORED RESEARCH

This invention was made with Government support under Grant No. R01NS088040 awarded by the National Institute of Health/National Institute of Neurological Disorders and Stroke. The Government has certain rights in this invention.

FIELD OF THE DISCLOSURE

The present disclosure relates generally to magnetic resonance imaging ("MRI"), and more specifically, to exemplary embodiments of exemplary system, method and computer-accessible medium for determining one or more brain microstructure parameters from one or more diffusion magnetic resonance imaging ("dMRI") signal's rotational invariants.

BACKGROUND INFORMATION

An imaging paradigm of characterizing tissue structure at a micrometer level, orders of magnitude below MRI resolution, has emerged over the past decade. Based on non-invasive diffusion MRI, combined with biophysical modeling, it promises to quantify water fractions and diffusion coefficients inside and outside neurites (e.g., axons and dendrites). These parameters can serve as sensitive and specific metrics of tissue integrity, and can provide objective diagnosis of neurodegenerative diseases at the earliest stage. Practically, however, parameter estimation has remained challenging due to rich orientational structure of neurites in each imaging voxel.

Thus, it may be beneficial to provide an exemplary system, method and computer-accessible medium for determining brain microstructure parameters from dMRI signal's rotational invariants, which can overcome some deficiencies present in current MRI systems and in current image processing and image analysis tools.

SUMMARY OF EXEMPLARY EMBODIMENTS

To that end, exemplary system, method and computer-accessible medium for determining a plurality of tissue parameters of a tissue(s) can be provided using which, for example, information related to a plurality of diffusion rotational invariants contained within a diffusion magnetic resonance ("dMR") image(s) of the tissue(s) can be received, and the tissue parameters can be determined by determining a relation(s) between the diffusion rotational invariants (such as, but not limited to, diffusion signal moments), and a plurality of properties of the tissue(s). The relation(s) can be or include an exact relation. The number of tissue parameters can be based on a maximum order of the diffusion moments. For example, diffusion moments can be the coefficient of a power low expansion of the dMRI signal in a parameter proportional to a power of the applied diffusion-sensitizing magnetic-field gradients. The tissue parameters can be or include parameters of a single voxel in the dMR image(s), scalar tissue parameters and/or tensor tissue parameters. The tensor tissue parameters can be determined based on the scalar tissue parameters, the diffusion rotational invariants and the dMR signal expansion in the spherical harmonics basis. The scalar parameters can include (i) a diffusivity inside neurites of the tissue(s), (ii) the diffusivities outside the neurites (such as, but not limited to, the diffusivity in parallel direction and the diffusivity in the perpendicular direction to the neurites), (iii) a neurite water fraction of the tissue(s) and/or (iv) an orientation distribution function of the neurites in the tissue(s). An activation of a magnetic resonance imaging apparatus can be caused in order to acquire the dMR image(s).

One exemplary relation can be based on a tensor(s) constructed from the dMR image(s). In some exemplary embodiments of the present disclosure, the tensor(s) can be a symmetric trace-free tensor(s). An activation of a magnetic resonance imaging apparatus can be caused in order to acquire the dMR image. According to a further exemplary embodiment of the present disclosure, system, method and computer-accessible medium can be provided for determining a plurality of tissue parameters of a tissue(s), using which, for example, it is possible to receive information related to a plurality of diffusion moments contained within a diffusion magnetic resonance (dMR) image(s) of the tissue(s), and generate the tissue parameters. The exemplary tissue parameters can be generated by factorizing a response of an individual fiber segment of the tissue(s) based on the set of rotational invariants constructed from the diffusion moments. The response of the individual fiber segments can be factorized from an orientation distribution function ("ODF"). The set of moments can be of a rotation group SO(3). The scalar tissue parameters can then be estimated from the response of the individual fiber segments.

According to a further exemplary embodiment of the present disclosure, system, method and computer-accessible medium can be provided for determining a plurality of tissue parameters of a tissue(s), using which, for example, it is possible to receive information related to a plurality of diffusion rotational invariants contained within a diffusion magnetic resonance (dMR) image(s) of the tissue(s), and generate the tissue parameters using a set of rotational invariants. The exemplary tissue parameters can be generated by factorizing a response of an individual fiber segment of the tissue(s) based on the set of rotational invariants. The response of the individual fiber segments can be factorized from an orientation distribution function ("ODF"). The set of rotational invariants can be of a rotation group SO(3). The scalar tissue parameters can then be estimated from the response of the individual fiber segments.

In some exemplary embodiment of the present disclosure, the first information can be estimated using a plurality of either cumulant or moment tensors determined from dMRI images. The tissue parameters can be generated using a non-linear fitting procedure(s), which can include, a minimization function(s). The tissue parameters can be generated using the minimization function(s) with respect to a plurality of model parameters. The tissue parameters can include at least two branches of tissue parameters, where one of the branches can be selected based on prior information about a range of model parameters values. The non-linear fitting procedure(s) can be based on a prevalence method, where a number of random initializations in each voxel can be used, and the fit outcome in each voxel can be selected by clustering the most prevalent outcomes from these random initializations. The non-linear fitting procedure can be also initialized based on the linear exemplary relation between the signal's moments and tissue parameters, and/or based on a duality transformation of the diffusion moments. The ODF can be constructed using a factorization relation. The relation(s) can be an exact relation.

In certain exemplary embodiments of the present disclosure, the number of the tissue parameters can be based on a maximum order of the diffusion moments. A plurality of tensor tissue parameters can be determined based on the scalar tissue parameters and the diffusion moments. The scalar parameters can include (i) a diffusivity inside neurites of the tissue(s), (ii) the diffusivities outside the neurites, (iii) a neurite water fraction of the tissue(s) and (iv) an orientation distribution function of the tissue(s). An activation of a magnetic resonance imaging apparatus can be caused or initiated in order to acquire the dMR image.

In some exemplary embodiments of the present disclosure, a signal(s) related to the dMR image(s). The rotational invariants can be constructed based on the dMR signal(s). A training set(s) (e.g., a synthetic data raining set(s)) can be generated, which can be used to generate the tissue parameters.

According to a further exemplary embodiment of the present disclosure, system, method and computer-accessible medium can be provided for determining a plurality of tissue parameters of a tissue(s), using which, for example, it is possible to receive information related to a plurality of diffusion rotational invariants contained within a diffusion magnetic resonance (dMR) image(s) of the tissue(s), and generate the tissue parameters using a set of rotational invariants by applying modern machine-learning methods, for example, employing Bayesian framework. Tissue parameter estimation can be performed in the space of rotational invariants generated from the acquired dMR images, by mapping the possible combinations of tissue parameters onto the set of rotational invariants (e.g., "training") and subsequently applying this mapping to the rotational invariants derived from the measured signal.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 2A-2D are graphs illustrating the problem of the low-energy landscape of parameter estimation;

FIG. 7A is a set of images of branch selection and relations between scalar parameters based on prevalence maps according to an exemplary embodiment of the present disclosure;

FIG. 7B is a set of histograms of branch selection and relations between scalar parameters based on prevalence maps according to an exemplary embodiment of the present disclosure;

FIG. 7C is a set of graphs of branch selection and relations between scalar parameters based on prevalence maps according to an exemplary embodiment of the present disclosure;

FIGS. 10A-10G are exemplary maps of correlation statistics of determined microscopic parameters with ground truth according to an exemplary embodiment of the present disclosure;

FIGS. 11A, 11B, 11D, and 11E are exemplary graphs illustrating overall errors in parameters according to an exemplary embodiment of the present disclosure;

FIGS. 11C and 11F are exemplary graphs illustrating errors in parameters as a function of the number of rotational invariant features according to an exemplary embodiment of the present disclosure;

FIG. 12A is a set of maps of microscopic parameters based on the Bayesian/machine learning approach according to an exemplary embodiment of the present disclosure;

FIG. 12B is a set of exemplary graphs illustrating the distribution of the parameters from FIG. 12A according to an exemplary embodiment of the present disclosure;

FIG. 12C is an exemplary graph illustrating the distribution of the normalized log-likelihood within white matter according to an exemplary embodiment of the present disclosure;

FIG. 14A is a set of exemplary images showing a comparison of intraaxonal fraction estimated using the exemplary system, method and computer-accessible medium according to an exemplary embodiment of the present disclosure;

FIGS. 14B and 14C are exemplary graphs illustrating a comparison of intraaxonal fraction estimated using the exemplary system, method and computer-accessible medium according to an exemplary embodiment of the present disclosure;

FIG. 15A is a set of exemplary images of microscopic parameters for a 2-shell60 protocol according to an exemplary embodiment of the present disclosure;

FIGS. 15B and 15C are exemplary graphs of microscopic parameters for a 2-shell60 protocol according to an exemplary embodiment of the present disclosure;

FIG. 16A is a set of images of a brain acquired using a hex28 protocol with a single measurement according to an exemplary embodiment of the present disclosure;

FIG. 16B is a set of exemplary images of a brain acquired using a hex28 protocol with three measurements according to an exemplary embodiment of the present disclosure;

FIG. 16C is a set of graphs illustrating parameter distributions for FIGS. 16A and 16B according to an exemplary embodiment of the present disclosure;

Figure 1:
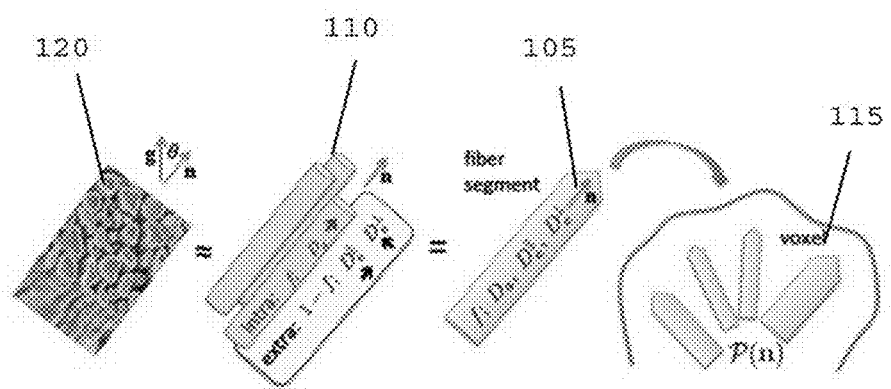
FIG. 1 is a diagram of a standard model of diffusion in the brain.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium, according to an exemplary embodiment of the present disclosure, can resolve the parameter estimation problem by employing a set of rotational invariants of the SO(3) group, thereby factorizing the response of an individual fiber segment (e.g., fascicle) from a complex neurite orientational distribution function ("ODF"). This factorization can simplify the parameter estimation problem by splitting it into two or more parts, and can facilitate the estimation of the response of an individual fiber segment, and then calculate the corresponding neurite fiber ODF.

Based on the exemplary rotational-invariant approach, various procedures can be used to estimate the scalar parameters of the fiber segments and the tensor parameters of the ODF for every imaging voxel in the brain and, more generally, in the nervous system, or in any tissue with a fibrous tissue structure (e.g. muscle).

At low diffusion weighting, the exact relations between the Taylor-expanded rotational invariants and tissue parameters can be derived. These relations (e.g., herein referred to LEMONADE) can yield the two distinct branches of parameters, which can describe the measurement equally well up to the 4th-order moments of the signal; the sixth-order moment, estimated from the measurement, can determine the branch and the solution for model parameters in the correct branch.

A full set of rotational invariants ("RotInv") that can be valid for any diffusion weighting, can be derived by the exemplary system, method and computer-accessible medium, and can be used to match with those identified from the measured signal, via, for example, nonlinear fitting using, (e.g., gradient-descent method). Thus, nonlinear fitting can be employed in the space of rotational invariants (e.g., "signal features") rather than in the space of all measurements, radically simplifying the estimation problem. The fitting can be either initialized using prior knowledge of the branch and/or of parameter values, or used multiple times from random initializations in order to select the most prevalent solution in each voxel.

Instead of the nonlinear fitting, modern machine-learning methods, for example, employing Bayesian framework, can be used to perform parameter estimation in the space of rotational invariants, by mapping the possible combinations of tissue parameters onto the set of rotational invariants (e.g., "training") and subsequently applying this mapping to the rotational invariants derived from the measured signal.

Most or all of these classes of methods can rely on the factorization between the fiber segment response and the fiber ODF, and the construction of rotational invariants based on this factorization. The exemplary system, method and computer-accessible medium, according to an exemplary embodiment of the present disclosure, can use multiple procedures, in combination with each other, such as using the outcome of the LEMONADE framework or of the Bayesian machine-learning method to initialize the nonlinear fitting for an improved precision and/or accuracy.

All exemplary procedures can rely on resolving the degeneracy of parameter estimation, for example, the observation (e.g., derived within the LEMONADE framework) that multiple sets of plausible parameters can approximate the measurement equally well. Thus, the exemplary system, method and computer-accessible medium, according to an exemplary embodiment of the present disclosure, can be used in combination with prior knowledge, established using a dedicated acquisition, regarding which part of the parameter space can contain the biophysically correct solution. Therefore, the branch selection can aid in narrowing down the parameter search domain for clinical acquisitions.

The outcome of the processing pipeline based on the exemplary system, method and computer-accessible medium can be a set of parametric and orientational maps in the whole brain, including regions of gray matter and crossings of white matter tracts. The exemplary framework can uncover rich microstructural content of a magnetic resonance image ("MRI") signal, and can bridge the gap between modern biophysical modeling and clinical MRI.

The "Standard Model" of water diffusion MRI ("dMRI") in the neuronal tissue can correspond to the physical picture (see, e.g., FIG. 1, References 1-8) of narrow impermeable neurites that can be embedded in the extra-neurite space (e.g., realistic tissue image 120). Elementary fiber segments 105, consisting of intra- and extra-neurite compartments 110, can be described by at least 4 independent parameters. Within a macroscopic imaging voxel 115, such segments can contribute to the directional dMRI signal according to their ODF $\mathcal{P}(\hat{n})$. Due to its rich orientational content, the total number of parameters characterizing a voxel can range between about 30-50, making direct nonlinear fitting of Eqs. (1) and (2) (written below) to noisy data impractical.

At sufficiently long (e.g., clinical) diffusion times t of approximately 10-100 ms, non-Gaussian effects (see, e.g., References 9 and 10) in each of the tissue compartments become small, which can facilitate parametrizing the acquisition by the diffusion weighting $b = q^2 t$. Thus, when measured in the unit direction g, the dMRI signal can be, for example:

$$S_{\hat{g}}(b) = \int_{|\hat{n}|=1} d\hat{n}\, \mathcal{P}(\hat{n}) \mathcal{K}(b, \hat{g}\cdot\hat{n}) \qquad (1)$$

and can be a convolution (e.g., on a unit sphere) between the fiber ODF $\mathcal{P}(\hat{n})$, and the response can be, for example:

$$\mathcal{K}(b,c) = f e^{-bD_a c^2} + (1-f) e^{-bD_e^{\perp} - b(D_e^{\parallel} - D_e^{\perp})c^2} \qquad (2)$$

from a perfectly aligned fiber segment (e.g., fascicle) pointing in the direction $\hat{n}$. The kernel (Eq. (2)) can depend on the relative angle, $\cos\theta \equiv c = \hat{g}\cdot\hat{n}$. It can be a sum of the exponential contributions from neurite and extra-neurite spaces, with water fractions f and 1−f, and the diffusion coefficients $D_a$ (e.g., inside) and $D_e^{\parallel}$, $D_e^{\perp}$ outside of the axons (e.g., neurites). Other compartments, for example, isotropic ones such as cerebrospinal fluid ("CSF") with volume fraction $f_{iso}$, can be added to the kernel in Eq. (2). Thus, for example:

$$\mathcal{K}(b,c) = fe^{-bD_a c^2} + (1-f-f_{iso})e^{-bD_e^{\perp}-b(D_e^{\parallel}D_e^{\perp})c^2} + f_{iso}e^{-bD_{iso}} \quad (3)$$

The kernel and the ODF parameters can carry distinct biophysical significance. Deconvolving voxel-wise fiber ODFs, instead of relying on the empirical directions from the signal (Eq. (1)), can provide a much more adequate starting point for the fiber tractography; an essential tool in pre-surgical planning. The kernel parameters can make dMRI measurements specific to μm-level disease processes, such as demyelination (see, e.g., Reference 11) ($D_e^{\perp}$), axonal loss (f), and axonal beading and inflammation (e.g., $D_a$ and $D_e^{\parallel}$). Since the diffusion coefficient can strongly depend on the packing geometry of restrictions (see, e.g., References 9-13), a simple mean-field relation between f and $D_e^{\perp}/D_e^{\parallel}$ does not hold (see, e.g., Reference 13) at the realistic tight axonal packings. Generally, to become specific to pathology, all the kernel parameters and the ODF may need to be determined separately.

How many parameters $N_p$ is it realistic to estimate from Eq. (1)? The answer depends on the maximal power $l_{max}$ of the diffusion weighting $q^{l_{max}}$ to which an acquisition can be sensitive, at a given signal-to-noise ratio ("SNR"). If the Taylor expansion of the signal, Eq. (1), can be considered in the fully symmetric moments $M_{i_1 \ldots i_l}^{(l)}$, for example:

$$S(b, \hat{g}) = 1 - bM_{i_1 i_2}^{(2)} g_{i_1} g_{i_2} + \frac{b^2}{2!} M_{i_1 \ldots i_4}^{(4)} g_{i_1} \ldots g_{i_4} - \quad (4)$$

where Einstein's convention of summation over pairs of repeating indices can be assumed, and the highest-order moment $M^{(l_{max})}$ still resolvable from the signal can set the maximal order $l_{max}$ for the even-order spherical harmonics ("SH") expansion of the ODF $\mathcal{P}(\hat{n}) = 1 + \Sigma_{l=2, 4 \ldots}^{l_{max}} \Sigma_{m=-l}^{l} p_{lm} Y_{lm}(\hat{n})$. Thus, the 4 scalar parameters from the kernel (e.g., Eq. (2)) can be complemented by the $n_c(l_{max})-1$ tensor parameters $p_{lm}$, where $n_c(l)=(l+1)(l+2)/2$, which can yield $$n_p(l_{max}) = 4 + \frac{l_{max}(l_{max}+3)}{2} = 9, 18, 31, 48, \ldots$$

for $l_{max} = 2, 4, 6, 8, \ldots$.

This exemplary parameter counting can reveal that the model complexity can grow fast, as $l_{max}^2$, due to the rich orientational content of the realistic fiber ODFs in the brain. As $l_{max} \sim 4-8$, dMRI signal can contain a few dozen parameters. Because of such high dimensionality of parameter space, direct nonlinear fitting of Eqs. (1) and (2) to realistic noisy data has been extremely non-robust. Thus, contrary to high-quality postmortem data (see, e.g., Reference 4), parameter estimation from clinical acquisitions has thus far reverted to making severe restrictions on the ODF shape; either assuming a highly aligned bundle (see, e.g., References 6 and 7), or a special Gaussian-like ODF shape; characterized by one (see, e.g., Reference 8) or two (see, e.g., Reference 14) parameters. Even assuming a 1-parameter ODF shape (see, e.g., Reference 8), unconstrained nonlinear fitting has revealed multiple biophysically plausible minima in the (4+1)-dimensional parameter space and shallow directions along them. (See, e.g., Reference 15). Current clinical data has been mostly analyzed by fixing all three diffusion coefficients and the ODF shape (see, e.g., Reference 8), introducing an a priori unknown bias (see, e.g., Reference 15) for the remaining few estimated parameters and heavily reducing specificity—the most lucrative feature of the microstructural modeling.

Exemplary Rotational Invariants

The exemplary system, method and computer-accessible medium, according to an exemplary embodiment of the present disclosure, can estimate all the parameters of the problem (see e.g., Eq. (1)) without making any assumptions on the ODF shape, and on the parameter values of the kernel $\mathcal{K}$. The exemplary approach can be based on the factorization between the ODF and the kernel in the spherical harmonics (SH) basis $Y_{lm}$. Since the kernel (see e.g., Eqs. (2) and (3)) can be axially symmetric, it can be expanded in even-order Legendre polynomials $P_l(c)$ only (e.g., in the m=0 SHs). Thus, for example:

$$\mathcal{K}(b, c) = \sum_{l=0,2,\ldots} (2l+1) K_l(b) P_l(c). \quad (5)$$

$$K_l(b) \equiv \int_0^1 dc \, \mathcal{K}(b, c) P_l(c). \quad (6)$$

Applying the SH addition formula $$P_l(\hat{g} \cdot \hat{n}) = \frac{4\pi}{2l+1} \sum_{m=-l}^{l} Y_{lm}(\hat{g}) Y_{lm}^*(\hat{n}) \quad (7)$$

can yield the following exemplary equation:

$$S_{lm}(b) = p_{lm} K_l(b) \quad (8)$$

where the SH components $S_{lm}$ of the dMRI signal can be determined in any suitable manner. Thus, for example:

$$S_{\hat{g}}(b) = \sum_{l=0,2,\ldots} \sum_{m=-l}^{l} S_{lm}(b) Y_{lm}(\hat{g}). \quad (9)$$

By introducing signal and ODF invariants $S_l \equiv \|S_l\|/N_l$ and $p_l \equiv \|p_l\|/N_l$ for each SO(3) irreducible representation labeled by "angular momentum" index l, where $\|S_l\|^2 = \Sigma_m S_{lm}^2$, $\|p_l\|^2 = \Sigma_m p_{lm}^2$, and where normalization $N_l = \sqrt{4\pi(2l+1)}$ can be chosen so that $0 \leq p_l \leq 1$, ODF can be factored out. Thus, for example:

$$S_l(b) = p_l K_l(b), \, l = 0, 2, 4, \ldots \quad (10)$$

and thereby first estimate the scalar parameters of the kernel $\mathcal{K}$, together with just a few $p_l$, from the reduced system of Eq. (10), one for each l. This can facilitate subsequent evaluations of the remaining $\sim l_{max}^2$ ODF coefficients $p_{lm}$ using Eq. (8), based on the estimated $S_{lm}$ from the measured signal (e.g., in a in a linear way).

For example, $p_l$ can be factored out by normalizing $S_l(b)$ by $\Sigma_{b_j} S_l(b_j)$ for each l, thereby fully factorizing the ODF; this strategy can be employed in the Bayesian approach described below.

The exemplary nonlinear parameter estimation problem based on the system (see e.g., Eq. (10)), can be equivalent to minimization of the "energy" function (e.g., with weights $w_{l,j}$). Thus, for example:

$$F^2(x) \equiv \frac{1}{(1+L/2)N_b} \sum_{l=0,2,...}^{L} \sum_{j=1}^{N_b} w_{l,j} [S_l(b_j) - p_l K_l(b_j)]^2 \quad (11)$$

with respect to $x = \{f, D_a, D_e^{\parallel}, D_e^{\perp}, p_l\}$, can still be nontrivial. Here $b_j$ can be the radii of $N_b$ shells in the q-space; assuming spherical sampling. The contour plots of F-values, shown in FIGS. 2A-4 for unit weights $w_{i,j}=1$, illustrate that the minimization landscape can generally be shallow (e.g., flat) in at least one dimension, and there can be multiple minima, even in the noise-free case.

Exemplary Expansion in Moments (LEMONADE)

For low enough b, nonlinear fitting (minimization of Eq. (11) practically can correspond to matching the first few moments of the signal (see e.g., Eq. (4)) to those of the exemplary model (see e.g., Eq. (1)). This matching can be derived below. These relations can facilitate the understanding of the topology of the low-energy landscape of F, and to speed up its minimization. The low-energy, also referred to as the maximum likelihood, includes expressing a high similarity between the model signal for given microstructural parameters and the measured signal Taking the L=0 invariant alone (e.g., equivalent to the isotropic signal averaging) (see e.g., Eqs. (17a)-(17g) below) up to $\mathcal{O}(b^2)$, can yield a two-dimensional surface, in accord with the two constraints of Eqs. (17a) and (17c) for the 4 scalar parameters $\{f, D_a, D_e^{\parallel}, D_e^{\perp}\}$, in good numerical agreement with the graph in FIG. 2A. Including the $K_2(b)$ invariant, L=2, can turn the surface into the two narrow one-dimensional trenches in the parameter space (e.g., the first 4 constraints of the system shown in Eqs. (17a)-(17g) for the above 4 parameters and $p_2$). These trenches can be exactly derived as the two branches $f_\pm(p_2)$ of the quadratic Eq. (21) described below.

The graphs of FIGS. 2A-2D show contour lines for $\min_{(D_e^{\perp},p_2)} F(f, D_a, D_e^{\parallel})$, the two sets of ground truth values, with differing $D_e^{\perp}=0.8$ (top) and $D_e^{\perp}=0.4$. All or most of the units for diffusion coefficients and for 1/b here can be $\mu m^2/ms$. The two exact LEMONADE branches $\zeta=\pm$ of the system (17) up to $\mathcal{O}(b^2)$ are shown using lines 205 and 210; they can become disjointed depending on the ground truth values. (See, e.g., FIGS. 2C and 2D). Including large b can limit the landscape to the surface $f/\sqrt{D_a}=$const arising solely from intra-neurite space (Reference 16), whose projection is drawn as line 215.

Figure 3:
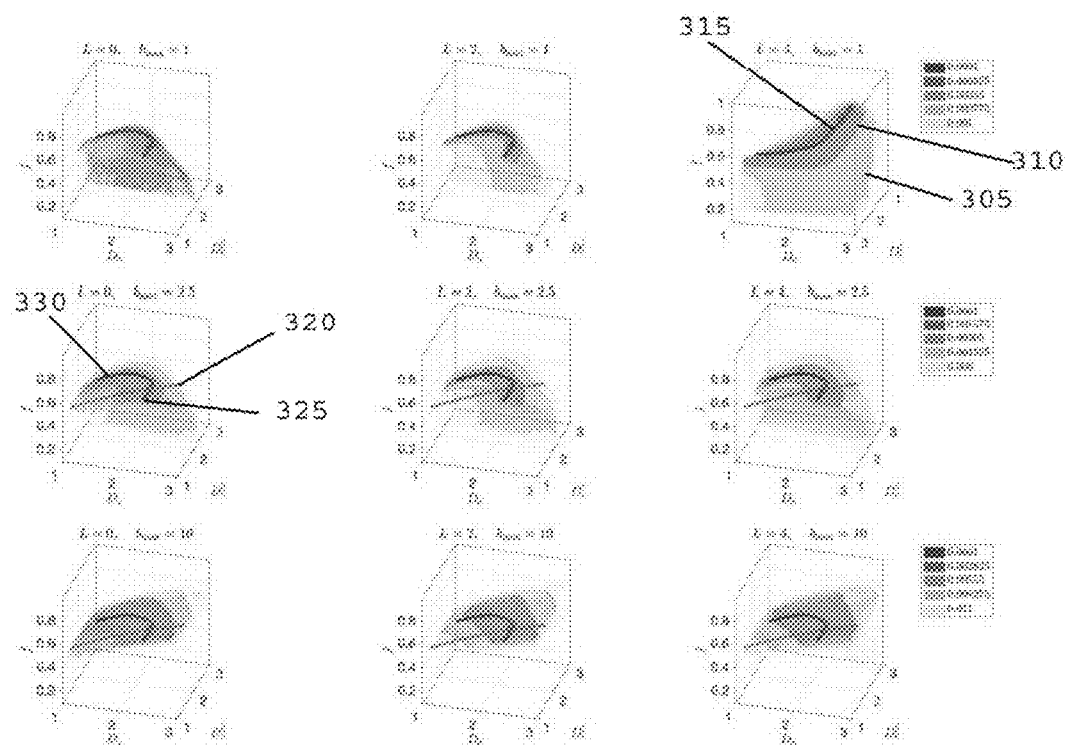
FIG. 3 is a set of graphs illustrating the low-energy landscape problem from FIGS. 2A-2D.

FIG. 3 shows a set of graphs of the low-energy landscape problem according to an exemplary embodiment of the present disclosure. The F-values (contours 305-315) can be minimized with respect to $D_e^{\perp}$ and $p_l$, for the case when the two branches form a single trench within the feasible parameter range. Ground truth values $\{f, D_a, D_e^{\parallel}, D_e^{\perp}, p_2\} = \{0.7, 2.4, 1.5, 0.8, 0.7\}$ here, as an illustration, correspond to three identical fiber segments crossing at an angle $\theta \approx 27°$ to the tract axis. The simulated b-values can correspond to those in human experiments, with all the 21 b-shells uniformly rescaled to attain the maximal value $b_{max}$. The two analytical LEMONADE branches 325 and 330 can match the low-value manifolds, especially for low $b_{max}$. Increasing L, the two-dimensional surface (L=0, corresponding to the two constraints in Eqs. (17a) and (17c) for 4 scalar parameters) gradually turns into one-dimensional trenches, while increasing $b_{max}$ can cause flattening of the landscape such that it eventually follows the surface $f/\sqrt{D_a}=$const dominated by the intra-axonal water (see, e.g., Reference 16), with the extra-axonal water exponentially suppressed (e.g., line 320, or line 430 in FIG. 4).

Figure 4:
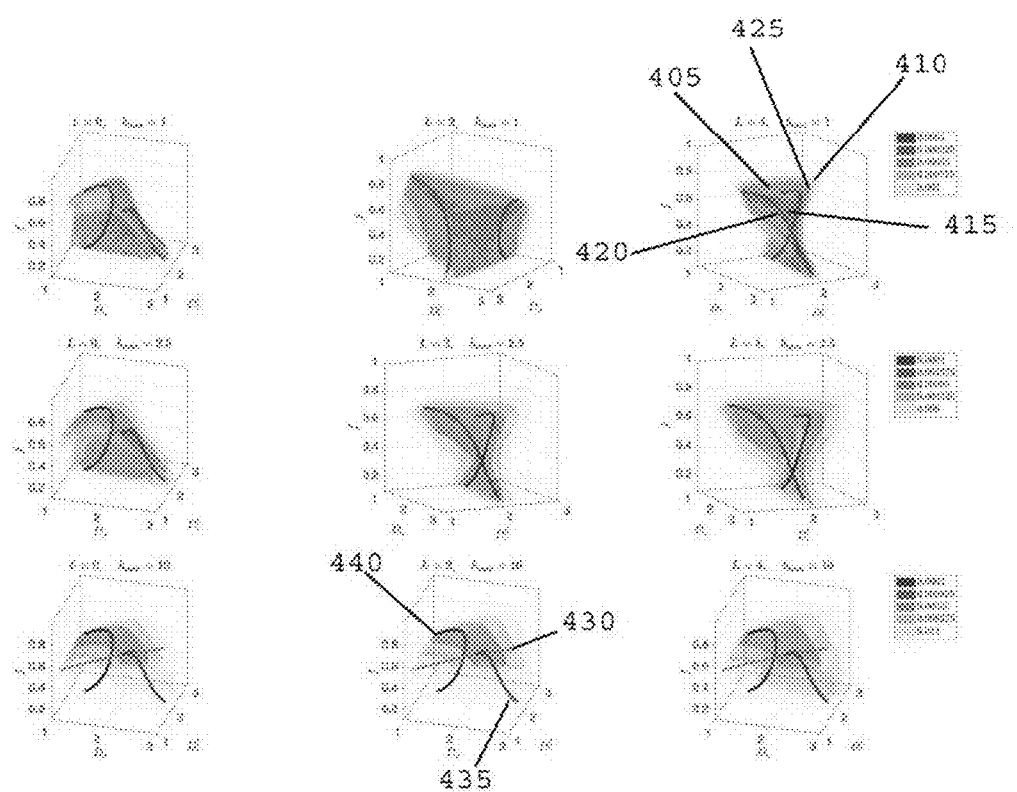
FIG. 4 is a further set of graphs illustrating the low-energy landscape problem from FIGS. 2A-2D where $D_e^\perp=0.4$.

The graphs shown in FIG. 4 are similar to those shown in FIG. 3, except that $D_e^{\perp}=0.4$. The landscape (contour lines 405-420) is highly sensitive to the ground truth values. Merely altering one parameter, $D_e^{\perp}$, two separate trenches (e.g., 435 and 440) can pass through the physically feasible parameter range. They eventually can connect (e.g., as in FIG. 3), albeit outside this range. In this exemplary case it can be particularly easy for spurious minima (e.g. due to noise) to appear in-between the trenches.

If the exemplary acquisition may only be sensitive to the order $\mathcal{O}(b^2)$, due to b-range and SNR limitations, the parameter estimation problem can be doubly degenerate, as can be empirically observed for a particular ODF shape (see, e.g., Reference 15): with respect to selecting the trench, and due to the flatness of either trench. The exemplary system, method and computer-accessible medium, according to an exemplary embodiment of the present disclosure, can now establish that this degeneracy and flatness can originate from the fact that each point in either branch can exactly match the b and $b^2$ terms in the Taylor expansion (see, e.g., Reference 4). Thus, while the lowest two moment tensors contain $N_c(4)=21$ nonequivalent parameters (e.g., Eq. (13)), they may not be enough to determine the corresponding $N_p(4)=18$ model parameters, since the excess parameters over-determine the ODF, whereas the two-compartment kernel (see e.g., Eq. (2)) can be under-determined. This issue can become even more severe if the kernel has more than two compartments (see e.g., Eq. (3)). This means that diffusion kurtosis imaging ("DKI") (see, e.g., Reference 18) alone may not be enough to resolve two-compartment model parameters, unless $p_2$ can be fixed by the ODF shape (e.g. $p_2 \to 1$, aligned fibers, References 6 and 7).

Exemplary Branch Selection

Sensitivity to $\mathcal{O}(b^3)$ terms and beyond, can fix both the branch and the solution inside the correct branch. Practically, however, branch selection from realistic noisy data has proven quite challenging, since biophysically plausible solutions can often appear from both branches. $\zeta=+$branch corresponds to, for example:

$$4 - \sqrt{\frac{40}{3}} < \beta < 4 + \sqrt{\frac{40}{3}}, \beta = \frac{D_a - D_e^{\parallel}}{D_e^{\perp}}, \quad (12)$$

and the $\zeta=-$branch should be chosen otherwise. Branch choice can change if it can rely on the l>2 invariants, and can be derived in a similar way, for example, for the l=0 and l=4 invariants.

The branches can be stable in the following way. Using both Monte Carlo simulations and human MRI data, it has been consistently observed that, starting the gradient-descent nonlinear fitting from a given branch value (e.g., found from the LEMONADE system) using moments determined from the low b acquisition) predominantly returns the parameters corresponding to the same branch. (See, e.g., FIG. 5). A branch assignment can be similar to a discrete topological index; characterizing which part of the parameter space a given imaging voxel belongs to. The branch choice can be non-trivial because the value of the three diffusivities entering Eq. (12) is not known a priori; besides, these values can generally vary in different brain regions such that the branch selection can be region-dependent. Noise can affect the parameter values enough to switch the branch ratio β, especially due to the division by small and particularly imprecisely determined $D_e^\perp$.

Figure 5:
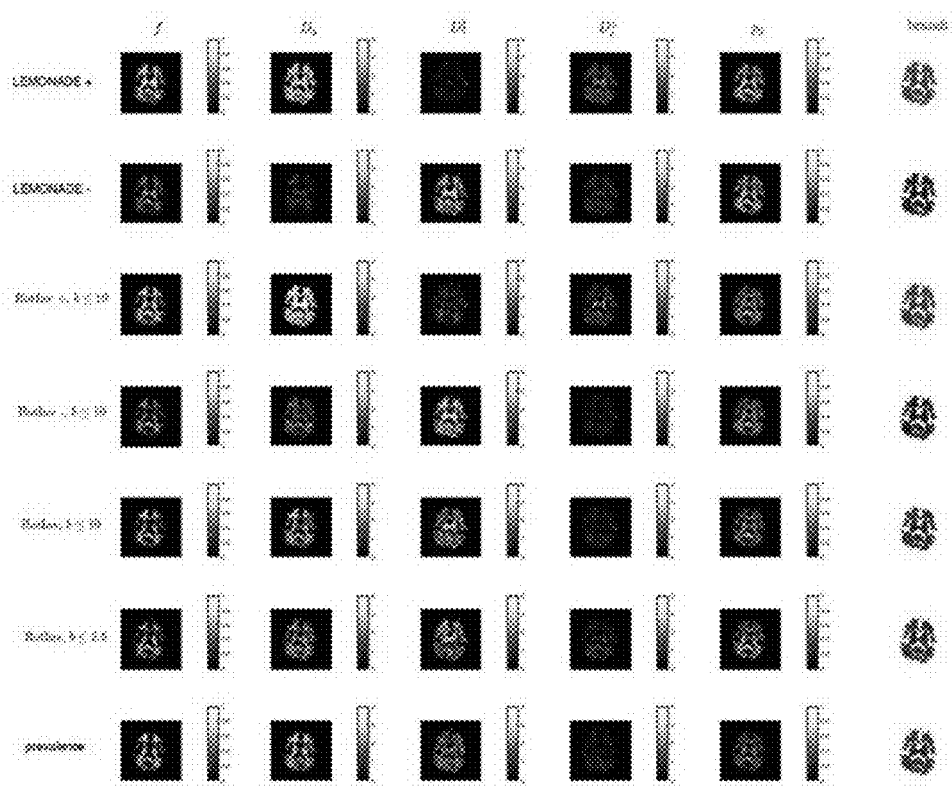
FIG. 5 is a set of exemplary brain maps according to an exemplary embodiment of the present disclosure.

Exemplary maps for the mid-brain slice of one subject are shown in FIG. 5. Rows 1 and 2 therein show outputs of LEMONADE ζ=±branches, Eqs. (17a)-(17g), using only the shells within 0≤b≤2.5. Note that $f_+>f_-$, as well as $D_{a+}>D_{e+}^\parallel$ and $D_{a-}<D_{e-}^\parallel$, practically consistent with Eq. (12). For the +branch, the output $D_e^\parallel<D_e^\perp$ can likely be a result of the bias of moments estimation (a similar bias was observed in numerical simulations), since it can be biophysically more plausible that $D_e^\parallel \gtrsim D_e^\perp$. Rows 3 and 4 of FIG. 5 show outputs of gradient-descent nonlinear minimization of the full rotational invariant estimation, Eq. (11) using all b shells, initialized via the corresponding LEMONADE maps. The same qualitative features as in the LEMONADE maps were observed, except for increasing $D_e^\parallel$ and decreasing $D_e^\perp$ for the +branch. The branch index can be stable—for the vast majority of voxels, the nonlinear fitting of the full problem (see, e.g., Reference 11) does not change the LEMONADE-assigned branch index ζ=±. Row 5 shows the combination of the ±RotInv maps using the +branch whenever parameters fall within plausible bounds, and -branch otherwise, generally resembles the prevalence maps (e.g., Row 7) for all estimated parameters in most of WM, as well as the corresponding branch index map ζ. Row 6 shows the combination of the ±RotInv maps, but now calculated only based on the 0≤b≤2.5 measurements, a proxy for the clinically feasible acquisition. While the results are noisier, the overall correspondence with the full acquisition is evident.

Exemplary Duality Transformation

The LEMONADE system of Eqs. (17a)-(17g), admitting the two solutions, can give rise to the duality transformation. From the combination $x=\{f, D_a, D_e^\parallel, D_e^\perp, p_2\}$ the moments $M^{(L),l}, l=0, 2$, can be calculated entering the left-hand side of Eqs. (17a)-(17g), from which the second, dual solution x* can be determined, with the property (x*)*≡x. Applying the duality relation can facilitate initializing the nonlinear fitting, by efficiently providing a potentially physically plausible starting point from a given fit outcome, and can facilitate identifying the correct branch locally.

Exemplary Bayesian/Machine Learning Procedure

A prior knowledge of the distribution of the model parameter values x can be assumed, which then can enable "training" the mapping between parameters x and rotational invariants (see e.g., Eq. (10)). This mapping can then be applied to the invariants $S_i(b)$ calculated from the data, to obtain x; alleviating the need for nonlinear fitting. This exemplary procedure can be also utilized in combination with nonlinear fitting, such as, but not limited to, providing an optimal initialization for the fit.

Exemplary Conclusions

By utilizing the SO(3) symmetry, the exemplary system, method and computer-accessible medium, according to an exemplary embodiment of the present disclosure, can factorize a previously unresolved parameter estimation problem for the neuronal tissue microstructure into the scalar and tensor (e.g., ODF) sectors. Taylor-expansion analysis of the scalar part can reveal nontrivial topology of the minimization landscape, with the first few moments exactly determining at least two narrow nearly-degenerate trenches along which the parameters approximate the measurement very well. The criterion (see e.g., Eq. (12)) for the branch selection can determine the parameter domain where the physical solution can be found. This selection can remain to be validated in animal studies and in human acquisitions using strong diffusion gradients or alternative acquisition procedures. However, in principle, the branch choice can be made for every voxel or brain region, once and for all. The exemplary combination of a linearized solution for the moments and the subsequent nonlinear fitting can give rise to an unconstrained procedure to provide parametric maps for the whole brain, already performing about two orders of magnitude faster than current methods (see, e.g., Reference 8) which employ constraints on kernel parameters, and on the ODF shape. Furthermore, application of machine learning/Bayesian procedures can facilitate even faster parameter estimation, in literally seconds (e.g., after training), provided the prior knowledge on the distributions of the parameter values exists. The exemplary analysis shows that often employed constraints between the scalar parameters (see, e.g. References 8 and 14), such as $D_a=D_e^\parallel$, or $1-f=D_e^\perp/D_e^\parallel$ generally do not hold, and can severely bias the remaining parameters due to the nontrivial topology of the minimization landscape. The exemplary system, method and computer-accessible medium, according to an exemplary embodiment of the present disclosure, can be free of these limitations, and can yield all the scalar (e.g., kernel) and tensor (e.g., ODF) parameters without such limiting assumptions.

Exemplary LEMONADE

Exemplary Expansion in the Moments. Parameter Counting.

The number of parameters of the moment's expansion (see, e.g., Eq. (4)) can be counted as a function of the maximal even order max. A term $M_{i_1 \ldots i_l}^{(l)}$ of rank l can be a fully symmetric tensor, which can be represented in terms of symmetric trace-free ("STF") tensors of rank l, l-2, . . . , 2, 0. Each set of STF tensors can realize an irreducible representation of the SO(3) group of rotations, equivalent (see, e.g., Reference 23) to the set of 2l+1 SH $Y_{lm}$. Thus, the total number of nonequivalent components in the rank-l moment can be $n_c(l)=\Sigma_{l=0, 2, \ldots}^{l}(2l+1)=\frac{1}{2}(l+1)(l+2)$. Truncating the series (4) at l=0, 2, . . . , $l_{max}$, can facilitate the determination of all components of $M_{i_1 \ldots i_l}^{(l)}$, for l=0, 2, . . . , $l_{max}$ with the total number of parameters being, for example:

$$N_c(l_{max}) = \sum_{l=2,4,\ldots}^{l_{max}} n_c(l) = \frac{1}{12} l_{max}^3 + \frac{5}{8} l_{max}^2 + \frac{17}{12} l_{max} \quad (13)$$

corresponding to $N_c$=6, 21, 49, . . . for $l_{max}$=2, 4, 6, . . . (e.g., the proton density $S_g(0)$ is not included in the exemplary counting). These can be the familiar numbers of DTI, DKI components, which can be determined linearly (e.g., robustly and quickly) from the measurement, using the b-matrix pseudoinversion.

Comparing $N_c(l_{max})$ with the corresponding number of model parameters $N_p(l_{max})$ determined after Eq. (4), it naively looks like the series (see, e.g., Eq. (4)) can be overdetermined, $N_c \geq N_p$, already for $l_{max} \geq 4$. As described below, it can be seen that all, or most, model parameters can be determined from the series (see, e.g., Eq. (4)) starting from $l_{max} \geq 6$, which can be a very important practical limitation for the parameter estimation. For $l_{max}$=4, there may not be enough equations for scalar model parameters, and too many for the tensor parameters $p_{lm}$.

To connect the moments to the model parameters, and to explore the low-energy landscape of the problem (see, e.g., Eq. (11)), the signal can be expanded. The $\mathcal{O}$ (b) term, l=2, can yield the diffusion tensor, which can be, for example:

$$M_{ij}^{(2)} = fD_a \langle n_i n_j \rangle + (1-f)(D_e^\perp \delta_{ij} + \Delta_e \langle n_i n_j \rangle) \tag{14a}$$

where $\langle n_i n_j \rangle = \int d\hat{n}\, P(\hat{n}) n_i n_j$ and $\Delta_e \equiv D_e^\parallel - D_e^\perp$. Expanding Eq. (1) up to $\mathcal{O}$ (b$^2$) and $\mathcal{O}$ (b$^3$) can yield the 4$^{th}$ and 6$^{th}$ order moments, for example:

$$M_{ijkl}^{(4)} = fD_a^2 \langle n_i n_j n_k n_l \rangle + \tag{14b}$$
$$(1-f)\left[D_e^{\perp 2}\delta_{ij}\delta_{kl} + 2D_e^\perp \Delta_e \langle n_i n_j \rangle \delta_{kl} + \Delta_e^2 \langle n_i n_j n_k n_l \rangle\right];$$

$$M_{i_1 \ldots i_6}^{(6)} = fD_a^3 \langle n_{i_1} \ldots n_{i_6} \rangle + \tag{14c}$$
$$(1-f)\left[D_e^{\perp 3}\delta_{(i_1 i_2}\delta_{i_3 i_4}\delta_{i_5 i_6)} + 3D_e^{\perp 2}\Delta_e \delta_{(i_1 i_2}\delta_{i_3 i_4}\langle n_{i_1} n_{i_6}\rangle) + \right.$$
$$\left. 3D_e^\perp \Delta_e \delta_{(i_1 i_2}\langle n_{i_3} \ldots n_{i_6})\rangle + \Delta_e^3 \langle n_{i_1} \ldots n_{i_6}\rangle \right].$$

Here symmetrization (see, e.g., Reference 23) over tensor indices between ( . . . ) can be assumed.

The exemplary system, method and computer-accessible medium, according to an exemplary embodiment of the present disclosure, can escalate the complexity by relating the higher-order moments of the signal to the nonlinear combinations of the scalar model parameters $\{f, D_a, D_e^\parallel, D_e^\perp\}$ and of the ODF averages $\langle n_{i_1} \ldots n_{i_l} \rangle = \int d\hat{n} P(\hat{n}) n_{i_1} \ldots n_{i_l}$. The above relations can be inverted in order to solve for the ODF expansion parameters $p_{lm}$ and the scalar model parameters in terms of the moments $M_{i_1 \ldots i_l}^{(l)}$, and to explore the properties of the exemplary solution.

Exemplary Scalar-Tensor Factorization for the Moments: Eq. (14) can provide an overdetermined nonlinear system for 31 model parameters. To obtain an exact solution, system symmetry can be used by working in the irreducible representations of the SO(3) group, for which this challenging problem can factorize. The SO(3) representations in Eq. (14) can be selected by projecting the products $n_{i_1} \ldots n_{i_l}$ onto the special STF tensors $\mathcal{Y}_{k_1 \ldots k_l}^{lm}$, (see, e.g., Reference 23), that can generate SHs. Thus, for example:

$$Y_{lm}(\hat{n}) = \mathcal{Y}_{k_1 \ldots k_l}^{lm} n_{k_1} \ldots n_{k_l}. \tag{15}$$

Since ODF can be real, $Y_{k_1 \ldots k_l}^{lm} \to \sqrt{2}\, \text{Re}\, Y_{k_1 \ldots k_l}^{lm}$ for m>0 and $Y_{k_1 \ldots k_l}^{lm} \to \sqrt{2}\, \text{Im}\, Y_{k_1 \ldots k_l}^{l|m|}$ for m<0, can be redefined to work in real SH basis. Introducing the corresponding moments in the SH basis, can produce, for example:

$$M^{(L),lm} = \frac{4\pi}{\mathcal{N}_l} \mathcal{Y}_{k_1 \ldots k_l}^{lm} \delta_{k_{l+1} k_{l+2}} \cdots \delta_{k_{L-1} k_{L-2}} M_{k_1 \ldots k_L}^{(L)}, \tag{16}$$

$M^{(L),lm}$ can be related to the model parameters by convolving Eq. (14) with $Y_{k_1 \ldots k_l}^{lm} \delta_{k_{l+1} k_{l+2}} \cdots \delta_{k_{L-1} k_L}$, and $\mathcal{N}_l = \sqrt{4\pi(2l+1)}$. As a result, the minimal system for $L \leq 6$ and l=0, 2 can be obtained. Thus, for example:

$$M^{(2),00} = fD_a + (1-f)(3D_e^\perp + \Delta_e) \tag{17a}$$

$$\frac{M^{(2),2m}}{p_{2m}/\mathcal{N}_2} = fD_a + (1-f)\Delta_e \tag{17b}$$

$$M^{(4),00} = fD_a^2 + (1-f)\left[5D_e^{\perp 2} + \frac{10}{3}D_e^\perp \Delta_e + \Delta_e^2\right] \tag{17c}$$

$$\frac{M^{(4),2m}}{p_{2m}/\mathcal{N}_2} = fD_a^2 + (1-f)\left[\frac{7}{3}D_e^\perp \Delta_e + \Delta_e^2\right] \tag{17d}$$

$$M^{(6),00} = fD_a^3 + (1-f)\left[7D_e^{\perp 2}(D_e^\perp + \Delta_e) + \frac{21}{5}D_e^\perp \Delta_e^2 + \Delta_e^3\right] \tag{17e}$$

$$\frac{M^{(6),2m}}{p_{2m}/\mathcal{N}_2} = fD_a^3 + (1-f)\left[\frac{21}{5}D_e^{\perp 2}\Delta_e + \frac{18}{5}D_e^\perp \Delta_e^2 + \Delta_e^3\right] \tag{17f}$$

The system of Eqs. (17a)-(17g) can involve minimal orders L and l enough to find all the 4 scalar kernel parameters and $p_2$. By defining $M^{(l),2} \equiv \|M^{(l),2m}\|$, and $p_2$ as defined before Eq. (10), the same system as in Eqs. (17a)-(17g) can be received, but with $M^{(l),2}/p_2$ on the left-hand side of Eq. (17b), (174) and (17f). The above system has 6 equations for 5 parameters; even if the isotropic (e.g. CSF) compartment, such as in Eq. (3), with its fraction and an isotropic Diso=$D_{CSF}$=3 μm²/ms were added, the 6 parameters can still be from an appropriately modified system. Having found the parameters of the kernel, the following exemplary equation can be produced:

$$M^{(l),lm} = \frac{p_{lm}}{\mathcal{N}_l}[fD_a^{l/2} + (1-f)\Delta_e^{l/2}] \tag{17g}$$

which can yield the ODF parameters $p_{lm}$ up to arbitrary order $l \leq l_{max}$, as long as $M^{(l),lm}$ can be linearly found from Eq. (16). Eqs. (17a) and (17g) can be equivalent to matching the Taylor expansion of Eq. (8), and to minimizing the expanded energy.

The exact relations (17a) and (17g) between the signal's moments $M^{(L),lm}$ in the SH basis, and the model parameters $f, D_a, D_e^\parallel, D_e^\perp, \Delta_e$ and $P_{lm}$ can be called "Linearly Estimated Moments provide Orientations of Neurites And their Diffusivities Exactly" ("LEMONADE").

Exemplary Lemonade Solutions: Low-Energy Branches. To solve the system, Eqs. (17a)-(17d) can be analyzed, and $D_a$, $D_e^\perp$ and $\Delta_e$ can be eliminated. Introducing the common scaling factor $$\overline{D}(p_2) \equiv \frac{1}{3}\left(M^{(2),00} - \frac{M^{(2),2}}{p_2}\right) = (1-f)D_e^\perp, \tag{18}$$

all quantities can be made dimensionless functions of $p_2$ and f. Thus, for example:

$$d_n \equiv \frac{D_a}{\overline{D}},\, d_2 \equiv \frac{M^{(2),2}}{p_2 \overline{D}},\, \delta_e \equiv \frac{\Delta_e}{\overline{D}} = \frac{d_2 - fd_n}{1-f}, \tag{19}$$

$$m_0 \equiv \frac{M^{(4),00}}{\overline{D}^2},\, m_2 \equiv \frac{M^{(2),2}}{p_2 \overline{D}^2},\, d_e^+ \equiv \frac{D_e^\perp}{\overline{D}} = \frac{1}{1-f},$$

such that moments $d_2$, $m_0$, $m_2$ can be functions of $p_2$ and $f = f(p_2)$. Thus, for example:

$$\Delta m(p_2) \equiv m_0 - m_2 = 5d_e^+ + \delta_e = \frac{5 + d_2 - fd_n}{1-f}. \tag{20}$$

Multiplying the dimensionless Eq. (17d) by f can produce the following exemplary equation:

$$fm_2 = (fd_n)^2 = f(d_2 - fd_n)\left[\frac{7}{3}\frac{1}{1-f} + \frac{d_2 - fd_n}{1-f}\right]$$

and eliminating $d_n$ using Eq. (20), the $f^3$ term can cancel, and the following exemplary quadratic equation can remain:

$$af^2 - (a + c - 40/3)f + c = 0, \quad (21)$$

where the functions $a = a(p_2)$ and $c = c(p_2)$ can be given by, for example:

$$a = (\Delta m)^2 - (7/3 + 2d_2)\Delta m + m_2, \quad c = (\Delta m - 5 - d_2)^2. \quad (22)$$

The exemplary LEMONADE system up to $\mathcal{O}(b^2)$ can yield two possible solutions $f = f_\pm(p_2)$, corresponding to the two branches of $\sqrt{\mathcal{D}}$, where the discriminant $\mathcal{D}$ of Eq. (21), expressed via the original parameters, using $c = f^2/(1-f)^2 \cdot (5 + d_2 - d_n)^2$ and $$a = \frac{c}{f} + \frac{40}{3}\bigg/(1-f),$$

can be a full square. Thus, for example:

$$\mathcal{D} = \left(a - c - \frac{40}{3}\right)^2 - \frac{160}{4}c \equiv \left(\frac{f}{1-f}\right)^2\left[(5 + d_2 - d_n)^2 - \frac{40}{3}\right]^2, \quad (23)$$

such that $$\sqrt{\mathcal{D}} = \eta \cdot \frac{f}{1-f}\left[(5 + d_2 - d_n)^2 - \frac{40}{3}\right],$$

and the sign $\eta$ of the expression in the [ ... ] bracket can be defined as, for example:

$$\eta \equiv \text{sgn}\left(|\beta - 4| - \sqrt{\frac{40}{3}}\right), \quad (24)$$

$$\beta = \frac{D_a - D_e^\parallel}{D_e^\perp},$$

For example, $5 + d_2 - d_n = 4 + (D_e^\parallel - D_a)/D_e^\perp$ can be used in terms of the original model parameters, independent of $f$. After expressing a and c in terms of the original model parameters, the correct solution $f_\zeta \equiv f$ can correspond to $\zeta\eta = -1$ sign choice for selecting the $\pm\sqrt{\mathcal{D}}$ term in the branch. Thus, for example:

$$f_\zeta(p_2) = (a + c - 40/3 + \zeta\sqrt{\mathcal{D}})/2a, \quad (25)$$

equivalent to the branch selection, Eq. (12) above.

A feature of the general solution can be the remaining dependence on $p_2$, due to the fiber orientation dispersion, leaving the model parameters undetermined at $\mathcal{O}(b^2)$; the branches $f_\pm(p_2)$ correspond to the two 1-dimensional manifolds of model parameters $\{f(p_2), D_a(p_2), D_e^\parallel(p_2), D_e^\perp(p_2), p_2\}_\pm$ that can exactly satisfy the first 4 equations of the system described in Eqs. (17a)-(17g). These manifolds can correspond to the two trenches in the low-energy landscape, Eq. (11), as shown in FIGS. 2A through 4, which can be flat if the exemplary acquisition may only be sensitive to $\mathcal{O}(b^2)$. It can be the $\mathcal{O}(b^2)$ terms, corresponding to Eqs. (17e) and (17f), that in the noise-free case select the correct trench (e.g., elevating F for the wrong one), and can yield the value $p_2$ fixing the minimum of F in the correct trench.

Once the branch index $\zeta = \pm$ can be fixed, substitution of Eq. (25) into the two (e.g., overdetermined) Eqs. (17e) and (17f) can yield $p_2$ and thus all scalar model parameters. The numerical solution can be fastest (e.g., approximately 1 millisecond/voxel on a desktop computer) by simply performing exhaustive search for the arg min of the sum of squares, or of any other combination, of Eqs. (17e) and (17f) on the discretized interval $0 \le p_2 \le 1$.

Exemplary Estimating Moments.

The cumulant tensors $C^{(l)}$ can be estimated as, for example:

$$\ln\frac{S_{\vec{g}}(b)}{S(0)} = -bC_{i_1 i_2}^{(2)} g_{i_1} g_{i_2} + b^2 C_{i_1 \ldots i_4}^{(4)} g_{i_1} \ldots g_{i_4} - \quad (26)$$

via linear matrix pseudoinversion of n $S_{\vec{g}}(b)$ with voxel-specific weights (see, e.g., Reference 22) up to, for example, $l_{max} = 6$. $C_{i_1 \ldots i_l}^{(l)}$ can be converted to the moments $M_{i_1 \ldots i_l}^{(l)}$ in an exemplary manner, (see, e.g., Reference 24) by adding the reducible parts from lower-order $C^{(l)}$. For an unbiased estimation, only shells within sufficiently low b, e.g. but not limited to, $0 \le b \le 2.5$ can be used, where the cumulant series converges.

Exemplary Nonlinear Fitting: Minimization of Function (11) with Respect to Model Parameters The application of nonlinear fitting approach can be shown on a dedicated measurement which took almost 2 hours. However, this method can be applied to any measurement, as can be shown by using only a low-b subset of the original data. To get the best possible proxy for the ground truth, and to select the branch, a dedicated dMRI acquisition was employed in the "extreme" range of b=0 . . . 10 ms/μm², as shown in FIGS. 5-7.

Exemplary MRI.

Three healthy volunteers underwent imaging on a Siemens Prisma 3T MR scanner, equipped with a 80 mT/m gradient system, after obtaining informed consent, using a 64-channel receiver head coil. The body coil was used for transmission. An EPI diffusion-weighted sequence was used to acquire the dMRI data. Diffusion weighting was applied along 64 isotropically distributed gradient directions for each of the 21 b-values that were equidistantly distributed in the range [0.10 ms/μm²]. The following imaging parameters were kept constant throughout the data acquisition sequence: TR/TE: 4000/105 ms, matrix: 80×80, NEX: 1, in-plane resolution: 3×3 mm², slice thickness: 3 mm, slices: 38, parallel imaging: GRAPPA with acceleration factor 2, reconstructed using the adaptive combine procedure to ensure Rician data distribution, multi-band acceleration with a factor of 2, and no partial Fourier.

Exemplary Image Processing.

MP-PCA noise estimation and denoising method (see, e.g., Reference 25) facilitated the preservation of the significant principal components and to strongly reduce the noise in the data and to estimate the noise map σ(x). The positive signal bias, inherent to low-SNR magnitude MR data, was removed by using the method of moments (see, e.g., Reference 26), where the denoised signal was used as a proxy for the Rician expectation value. Denoised and Rice-floor-corrected images were subsequently corrected for Gibbs ringing (see, e.g., References 27 and 28), geometric eddy current distortions and subject motion (see, e.g., Reference 29).

Figure 8:
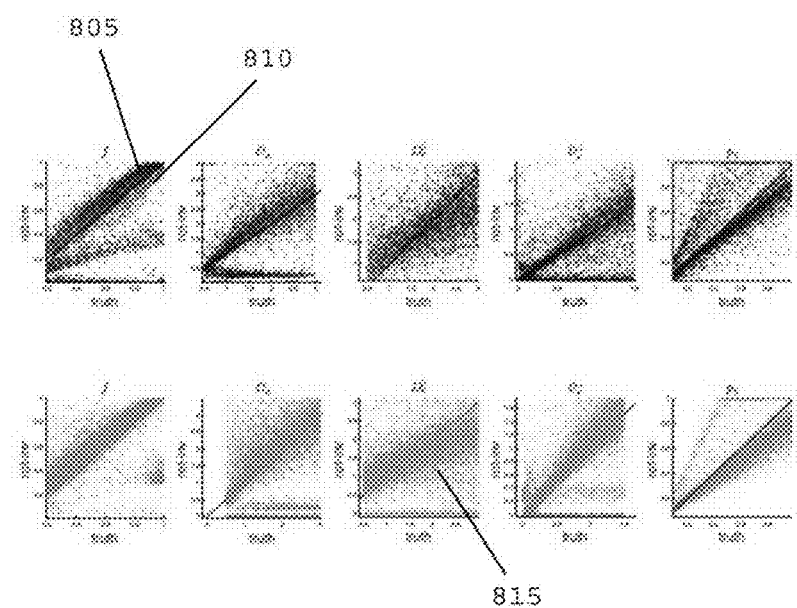
FIG. 8 is a set of graphs illustrating noise propagation according to an exemplary embodiment of the present disclosure.

After the denoising and Rician bias correction described above, the scalar parameters can be calculated independently of the branch location, solely based on the prevalence procedure. For each voxel, the problem can be initialized using, for instance, 20 random starting points within the biophysically plausible parameter range (e.g., 0<f, $p_2$<1, and 0<D<3 for all diffusivities). Observe that the fit outcome can typically cluster around a few points in the multi-dimensional parameter space, and select the predominant cluster can be selected (e.g., after excluding the outcomes outside the plausible bounds). The graphs shown in FIG. 8 illustrate the exemplary system, method and computer-accessible medium, according to an exemplary embodiment of the present disclosure, using simulations for a range of ground truth values with added substantial noise. The overall maps (e.g., FIG. 6B) look sufficiently smooth and biophysically plausible. The prevalence calculation for all three subjects was performed, and the prevalence maps were observed to be quite stable, by, for example, registering subjects 1 and 2 to subject 3 space and starting from the subjects 1 or 2 values to obtain the values very similar to the prevalence map of the subject 3.

FIG. 8 shows graphs of exemplary Monte Carlo simulations of the actual MRI protocol with 10,000 random combinations of ground truth uniformly distributed within the corresponding biophysically relevant intervals (x-axis). The fiber geometry is three identical fiber segments with azimuthal angles $\phi=0, \pm 2\pi/3$, crossing at an angle $\theta \approx 27°$ with respect to the tract axis. Rician noise is added with a SNR=33. Parameter estimation based on LEMONADE output served as initialization for the nonlinear fitting of Eq. (11), where the exemplary LEMONADE branch was pre-selected based on the ground truth values; branches are labeled as 805 and 810. It can be seen that the noise results in a decrease of the precision and that it can accidentally switch the branch. Generally, intra-axonal parameters $f$ and $D_a$ can be more precise than extra-axonal $D_e^{\parallel}$ and $D_e^{\perp}$. Parameter estimation can be done using the exemplary system, method and computer-accessible medium, by starting at 20 random initializations within the physically relevant domain of parameters as shown by element 815.

Exemplary Fiber ODF Calculation Using Factorization Relation from Eq. (10):

Empirical signal ODF using SH coefficients $p_{lm}=(-)^{l/2}S_{lm}$ (e.g., FIG. 6A), and the fiber ODF calculated using $p_{lm}$ from Eq. (10) (e.g., FIG. 6B), using the locally estimated kernel $K_f(b)$ (e.g., employing the scalar parameters), for the b=5 shell, with $1 \leq l_{max}=6$. Note the strong ODF sharpening effect due to the deconvolution with a locally estimated kernel $K_f(b)$.

The histograms of the branch ratio shown in FIG. 7B show that the −branch can dominate in GM, while +branch can prevail in WM. Voxels with $D_a \approx D_e^{\parallel}$ (e.g., that correspond to the discriminant $\mathcal{D} \to 0$ in the LEMONADE solution, and can be found starting from either branch) can be predominantly found in the posterior part of the brain. The scatter plots illustrated in FIG. 7C show that all kernel diffusivities should be estimated independently, since neither of the two widely employed constraints $D_a=D_e^{\parallel}$ and $D_e^{\parallel}=D_e^{\perp}/(1-f)$ can be valid. (See. e.g., References 8 and 14.)

FIGS. 7A-7C show exemplary illustrations and graphs of branch selection and relations between scalar parameters based on the prevalence maps (e.g., see FIG. 7A) for three subjects. Histograms of the branch ratio β and branch selection based on Eq. (12) show that the −branch 705 can dominate in the grey matter ("GM"), while the white matter ("WM") voxels can fall on either side of the branch choice, with the +branch (e.g., branch 710) dominant and spatially corresponding to regions around ventricles. (See, e.g., FIG. 7B). FIG. 7C shows that both widely used constraints (see, e.g., References 8 and 14), the mean-field tortuosity model $1-f=D_e^{\perp}/D_e^{\parallel}$, and $D_a=D_e^{\parallel}$, generally fail. All WM+GM voxels are shown (e.g., according to the probabilistic masks), confirming consistency of the prevalence parameter values between the subjects. The three clear domains correspond to those in the histograms.

The predominance of +branch in periventricular WM can prompt the following procedure: employ the outcome of +branch whenever the parameters fall within the biophysically plausible range, and −branch otherwise. Empirically, this can lead to the RotInv parametric maps very similar to the prevalence maps. (See, e.g., FIGS. 6A and 6B). Other, more involved branch identification procedures can be employed analogously to this one, based on our enhanced understanding about the local diffusivity values in every voxel and brain region.

The exemplary system, method and computer-accessible medium, according to an exemplary embodiment of the present disclosure, can formulate the branch selection as an essential problem for quantifying neuronal microstructure, to be resolved using acquisitions on scanners with very strong diffusion gradients (e.g., the Connectom scanner), as well as "orthogonal" acquisitions such as isotropic diffusion weighting. (See, e.g., References 19 and 20). While the latter recipe seems to produce relations $D_a \approx D_e^{\parallel}+2D_e^{\perp}$ due to a relatively small iso-weighted kurtosis (see, e.g., Reference 19) that can be interpreted as favoring the +branch in WM, this relation may not serve as a global constraint. (See, e.g., Reference 20)

Figure 6A:
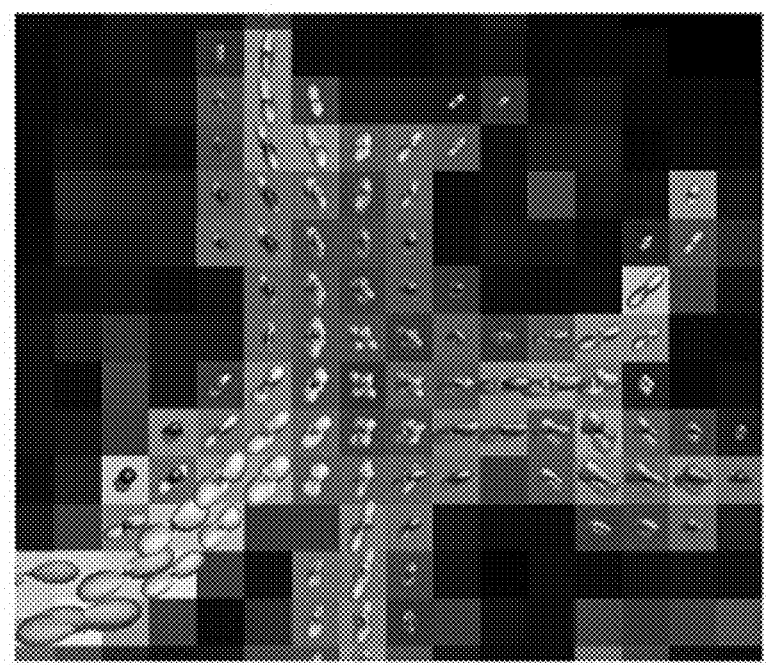
FIGS. 6A and 6B are exemplary images of an orientational distribution function reconstruction according to an exemplary embodiment of the present disclosure.
Figure 6B:
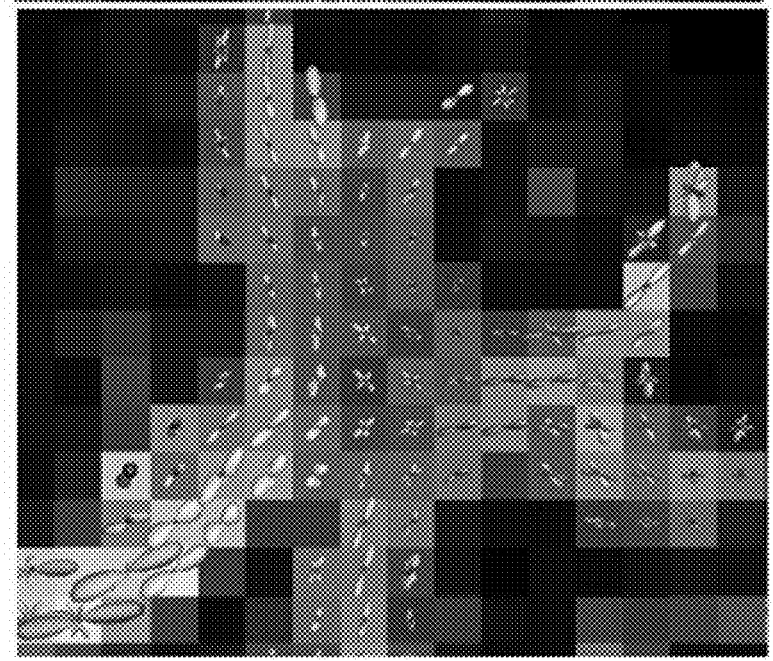

The fiber ODFs shown in FIGS. 6A and 6B, calculated using the factorization relation, can be notably sharper than the empirical signal ODFs, since dividing by the locally estimated kernel $K_f(b)$ can provide larger weight to the higher-order spherical harmonics. These ODFs can be a starting point for any standard fiber tracking procedure. These voxel-wise maps and ODFs can serve as a natural starting point for the mesoscopic global fiber tracking (see, e.g., References 21 and 30) that can provide further regularization of the parameter estimation problem by taking into account values in the adjacent voxels.

The computation time breakdown for the whole brain (e.g., 34,383 voxels within the WM+GM mask for subject 1) on a desktop iMac (e.g., 4 cores) can be as follows: under 2 min for estimating the cumulants using the b-matrix pseudo-inversion with the voxel-specific weights (see, e.g., Reference 22), together with recalculating the moments $M^{(L),lm}$ from the cumulants (e.g., only the range b≤2.5 was used for unbiased estimation); 1.5 min for LEMONADE calculation (e.g., both branches); and 4 min for the nonlinear fitting (e.g., both branches), using the corresponding LEMONADE solutions as fit initialization, employing the whole b range. Nonlinear fitting can achieve considerable speedup because of the initial values being already quite close to the minima of F; the corresponding integrals and their first derivatives in a broad range, can be pre-computed and/or interpolated.

Generalizing, for any number of compartments in the kernel, for example, Eq. (3) or its further generalizations onto adding other compartments or describing other fibrous tissues such as muscle, the scalar sector of the parameter estimation problem can provide an infinite set of rotational invariants, l=0, 2, . . . , which can be related to the kernel parameters irrespective of the basis and of the fiber ODF. The branch-selection degeneracy of the scalar sector can persist for 3 or more compartments. Relating rotational invariants of the moments to kernel parameters can be used to analyze this degeneracy. If the added compartment(s) can be isotropic, the exemplary LEMONADE branches can correspond to the anisotropic two-compartment part of the kernel K, determining the respective higher-dimensional "low-energy" manifolds in the parameter space. Procedure other than gradient descent can be utilized for minimizing the function in the physical parameter domain; applicability of any such procedures, in general, can depend on resolving the branch selection problem that can be region-of-interest and tissue dependent.

Exemplary Parameter Estimation Using Bayesian/Machine Learning

The following exemplary notation can be used below. $M(b) \equiv \mathcal{K}(b)$ can be denoted as any biophysical model for the microscopic tissue structure (e.g., an elementary fiber segment response, or kernel) entering Eq. (1). Thus, the three-compartment kernel reads can be, for example:

$$M(b,c) = v_i e^{-bD_\parallel^i c^2} + v_e e^{-bD_\perp - b(D_\parallel^e - D_\perp)c^2} + v_f e^{-bD_f} \qquad (27)$$

where D and v can describe the diffusivities and the volume fractions of the corresponding compartments. Thus, $f$ can now be $v_i$, $D_\parallel^i \equiv D_a$ can be the longitudinal intra-axonal diffusivity. The extra-axonal diffusivities can be $D_\parallel^e \equiv D_e^\parallel$ and $D_\perp \equiv D_e^\perp$ in the parallel and transverse directions, respectively; "free", or CSF, diffusivity can be set to $D_f = 3$ μm$^2$/ms, and $v_i + v_e + v_f = 1$, similar to Eq. (3) above. Summarizing, the model can include five independent microstructural parameters $x = \{v_i, v_e, D_\parallel^e, D_\parallel^i, D_\perp\}$.

Starting from the rotational invariants, the exemplary system, method and computer-accessible medium, according to an exemplary embodiment of the present disclosure, can operate with a set of ODF-independent rotational invariants, or "features" $f_l^b$, which can depend exclusively on the microstructure model (e.g., kernel) $M_l^b \equiv K_l(b)$. Thus, for example:

$$f_l^b := \frac{\sum_m |S_{l,m}^b|^2}{\sum_{m,b'} |S_{l,m}^{b'}|^2} = \frac{|M_l^b|^2}{\sum_{b'} |M_l^{b'}|^2} \qquad (28)$$

where the coefficients $S_{l,m}^b \equiv S_{lm}(b)$ from the SH expansion of the dMRI signal. The remaining ODF dependency through $p_l$ can be thus cancelled, as in Eq. (28) that does not contain $p_l$.

Figure 9A:
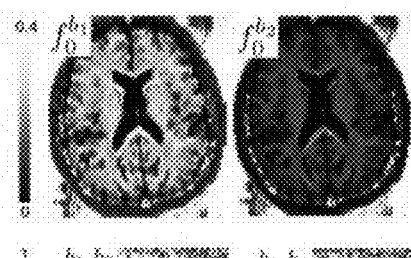
FIGS. 9A-9C are exemplary images illustrating rotational invariant features constructed from dMRI images of a transverse brain slice according to an exemplary embodiment of the present disclosure.
Figure 9B:
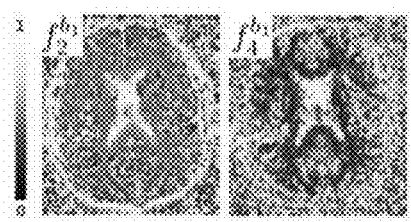
Figure 9C:
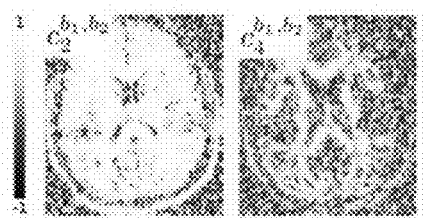

The exemplary features $f_l^b$ can reflect the anisotropy of the microscopic model, which may only be possible using l>0. Examples of feature maps obtained from experimental data are shown in FIGS. 9A-9C. For controlling the data quality, maps of the quantities can be calculated as, for example:

$$c_l^{b_1, b_2} = \frac{\sum_m S_{l,m}^{b_1} S_{l,m}^{b_2*}}{\sqrt{\sum_m |S_{l,m}^{b_1}|^2 \sum_m |S_{l,m}^{b_2}|^2}}. \qquad (29)$$

In principle, in an ideal noise-free measurement, $c_l^{b_1,b_2} = 1$ since the model parameters are real-valued. Noise can result in deviations from unity. Since the influence of the noise can increase with increasing l, monitoring the quantities $c_l^{b_1,b_2}$ can help select the values of l for which the features $f_l^b$ can be trusted. (See, e.g., FIGS. 9A-9C).

Exemplary Parameter Estimation Using Bayesian Approach.

The exemplary system, method and computer-accessible medium, according to an exemplary embodiment of the present disclosure, can map the features $f$ onto the microstructural (e.g., kernel) parameters (e.g., water fractions and compartment diffusivities), which can be denoted with x in the following. Instead of finding the most probable value for x given $f$, as performed in the conventional fitting, here the expectation value can be estimated as, for example:

$$\tilde{x}_B(f) = \int x p(x|f) dx \qquad (30)$$

of the posterior distribution $p(x|f)$. To find $\tilde{x}_B(f)$, the quadratic risk function can be minimized as, for example:

$$\tilde{x}_B(f) = \underset{\tilde{x} \in \text{fun}(X)}{\arg\min} \int (\tilde{x}(f) - x)^2 p(x, f) dx df \qquad (31)$$

where $p(x,f)$ can be the full joint generative model. It was found that simple polynomial regressors can be sufficient to represent the mapping $\tilde{x}_B(f)$. Thus, for example:

$$\tilde{x}(f) = \sum_{j_1 + \ldots + j_N \leq W} \beta_{j_1, j_2 \ldots j_N} f_1^{j_1} f_2^{j_2} \ldots f_N^{j_N} \qquad (32)$$

where the $\beta j_1, j_2 \ldots j_N$ can be the coefficients to be learned and W can be the maximal order of the polynomial. Such estimation can be integrated in Monte-Carlo fashion. Therein, the full signal formation process can be simulated using a specific tissue model including measurement noise. The set of samples drawn during Monte-Carlo integration can form the training data.

Exemplary Generating the Training Data.

The training examples can be simulated by following Eqs. (1) and (27) (e.g., with $\mathcal{K} \rightarrow M$) using a specific diffusion-weighting acquisition procedure (e.g., b-values and diffusion weighting directions g). Three exemplary acquisition procedures can be considered: (i) Human Connectome Project ("HCP"), WU-Minn consortium, (ii) in-house developed 2-shell60 and (iii) in-house developed hex28. More details about these data acquisition procedures are provided below.

In a first exemplary procedure, model parameters can be generated randomly and uniformly in biophysically plausible ranges, which can be $D_\parallel^i$, $D_\parallel^e$, ∈[0.2, 3]μm$^2$/ms and $D_\perp$∈[0.2, 1.5]μm$^2$/ms for the diffusivities. There can be different options for selecting compartmental volume fractions. Focusing on the intraaxonal volume fraction $v_i$ as a parameter suggests its uniform distribution in the interval [0, 1] as the most unbiased choice. The extraaxonal fraction $v_e$ can then be drawn uniformly from the interval [0, (1−$v_i$)] and the isotropic fraction can be determined by the normalization condition. By this exemplary procedure $v_e$ and $v_f$ can be distributed identically with mean ¼, while $v_i$ can be distributed uniformly with mean ½. Equal focus on the three volume fractions can suggest that their uniform distribution on the plane $v_i + v_e + v_f = 1$ can be limited to the octant of all positive v. This can provide the mean ⅓ for all volume fractions. The choice can have a minor effect on the microscopic parameters as shown below.

While the measurement can be a forward mapping of the model parameters to the features, $f(x)$, the existence of the inverse function may not be insured. A reduced model with $v_f=0$ can indicate a bimodality, as described above (e.g., the exemplary LEMONADE procedure from, Eqs. (17a)-(17g) and (21); this bimodality can persist in the nonlinear fitting, as also described above). Parameter combinations with $D_{\|}^i > D_{\|}^e$ and $D_{\|}^i < D_{\|}^e$ can describe noisy experimental data equally well (See, e.g., the exemplary two LEMONADE branches above, as well as Reference 15). This can imply that the conditional probability $p(f|x)$ can have at least two maxima and the function $f(x)$ may not be invertible. Selection of a single solution branch can be beneficial using additional biophysical information, as described above. The results of an isotropic weighting procedure (see, e.g., Reference 19) that can indicate a low kurtosis for the traces of intra- and extraaxonal diffusion tensors, can be used for at least a subset of brain voxels. Since kurtosis can be sensitive to the difference in diffusivities, the traces of the intra- and extraaxonal compartments can be selected to be similar, (e.g., $|D_{\|}^i - (D_{\|}^e + 2D_{\perp})| < 1.5 \ \mu m^2/ms$). However, discussed above, such constraint may not work globally (see, e.g., Reference 20); this branch selection/constraint can be established regionally via a highly dedicated measurement (e.g., as described herein).

Exemplary Training.

Construction of training signals can utilize a definition of mesoscopic structure. Different numbers of fibers (e.g., from one to thirty) can be generated with orientations drawn from the uniform angular distribution. Rician, or non-central, chi-distributed noise can be added to the signal depending on the MR-image reconstruction procedure used. As DWI images can show a spatially varying signal-to-noise ratio ("SNR"), a wide range of possible noise levels can be estimated. The exemplary system, method and computer-accessible medium, according to an exemplary embodiment of the present disclosure, can quantize SNR in 100 different levels, and can train them independently. During application to measured data, the exemplary system, method and computer-accessible medium, according to an exemplary embodiment of the present disclosure, can discretize the measured SNR levels (e.g., computed via the standard deviation of the b=0 images, or using the exemplary recent noise estimation method (see e.g., References 25 and 31)) and can apply the appropriate pre-trained Bayesian model, $\tilde{x}_B(f)$.

Exemplary Estimating Mesoscopic (Fiber ODF) Structure.

Once the microstructure can be determined, it can be beneficial to determine how well the microscopic parameters predict the raw signal. To perform this comparison, it can also be beneficial to estimate the mesoscopic structure, or the fiber ODF. In the following description, the following considerations are based on configurations with a single dominant fiber direction, an extension to multiple directions can be straightforward.

A fiber orientation dispersion model can be fit to the data, while keeping the already estimated microstructure parameters (e.g., of the kernel) fixed. However, to keep it efficient, the dispersion parameters can be estimated from low order spherical harmonic coefficients, such that no fitting or optimization can be beneficial. Suppose $M_l^b$ can be known, then $\kappa_l := \Sigma_{m,b} |S_{l,m}^b|^2 / \Sigma_b |M_l^b|^2$ can be an estimate for $\Sigma_m |p_{l,m}|^2$. In the case of axially symmetric dispersion with known direction (e.g., which can define the z-direction without reducing generality) only m=0 components can contribute, and $\kappa_l$ can become a direct estimate for $|p_l|^2 = |p_{l,0}|^2 = \kappa_l$ where $p_{l,0}$ can be real.

For common dispersion models, there can already be a one-to-one mapping of $\kappa_2$ onto the dispersion parameter. The Watson distribution and the Poisson kernel interpreted as a spherical probability distribution can be considered. For the Watson distribution, the mapping from $K_2$ onto the concentration parameter can be cumbersome, and there may be no closed form solution. For the Poisson kernel, the situation can be rather simple. In spherical harmonics, the Poisson kernel can have the form $p_l = \lambda^l$ with dispersion parameter $\lambda \in [0,1]$. The Poisson kernel usually does not appear as a probability distribution, but as the Green's function of the Laplace equation inside the ball. Its form in the angular domain can be, for example:

$$p(n_f \cdot n) = \Sigma_l \lambda^l P_l(n_f \cdot n) = (1 + \lambda^2 - 2\lambda(n_f \cdot n))^{-1/2}.$$

Exemplary Analysis of the Training Error.

Before processing experimental data, the overall performance of the exemplary system, method and computer-accessible medium can be determined by investigating the prediction error of the trained Bayesian model. This was evaluated for all involved protocols. (See, e.g., FIGS. 10A-10G). The number of acquired b-shells can determine the number of features. If the spherical harmonic index l can be restricted to be $l \leq 2$ (see, e.g., FIGS. 9A-9D), there can be 5 features for HCP, $f = \{f_0^1, f_0^2, f_0^3, f_2^1, f_2^2\}$, and 3 for the 2-shell60, $f = (f_0^1, f_0^2, f_2^1)$, as well as for hex28 as explained below.

Figure 9D:
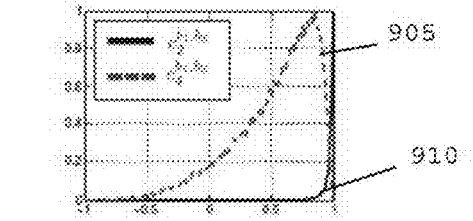
FIG. 9D is an exemplary graph illustrating features of a transverse brain slice according to an exemplary embodiment of the present disclosure.

Feature images $f_l^b$ of a transverse slice of the 2-shell60 protocol $$\left(b_1 = \frac{1 \text{ ms}}{\mu m^2}, b_2 = \frac{2 \text{ ms}}{\mu m^2}\right)$$

are shown in FIGS. 9A-9D. FIGS. 9C and 9D show the $c_l^{b_1,b_2}$ maps and histograms of the same slice together with their distribution within white matter. The histogram for $c_2$ (element 910) is nicely centered around unity, as expected for an ideal measurement, whereas the histogram for $c_4$ (element 905) is broad, which can indicate a reduced data quality for l=4.

FIGS. 10A-10G show correlation plots for the predicted parameters versus the ground truth for all protocols. The most advanced HCP acquisition for which the noise-free training results can be shown as well as for the more realistic SNR=20. The volume fractions can be estimated reliably for high-quality data, whereas the diffusivities can be noisier and biased for all data acquisition procedures. In the extreme case of completely insufficient data, the prediction can equal the mean of training data distribution, which can be nearly the case for $D_{\|}^e$ and $D_{\perp}$ for the 2-shell60 and hex28 protocols. Using a simpler model for the microstructure without a CSF compartment, $v_f=0$ can alleviate this problem, although it may not resolve it satisfactorily.

Correlation statistics of determined microscopic parameters with the ground truth on the training set for all three data acquisition protocols with the focus on the most acquisition-demanding HCP scheme are shown in FIGS. 10A-10D. This analysis can indicate insufficiency of all protocols for detecting all three microscopic diffusivities while the volume fractions can be determined. Training performed with $l_{max}=2$ and the polynomial order W=3 (e.g., Eq. (32) above).

To determine whether increasing $l_{max}$ or W can improve the results, their effect on the error on the whole training set can be shown. (See, e.g., FIGS. 11A-11F). The error can be calculated as the root mean squared deviation of the estimated parameters from the ground truth, and normalized on the analogous quantity for a fully uninformed guess for which the genuine value can be replaced with the mean of the parameter distribution in the training set. While such an error estimate can be unity for insufficient data, it can decrease with increasing W and $l_{max}$. For realistic SNR values, however, values of W and $l_{max}$=2 higher than 3 and 2, respectively, may not lead to significant improvement.

FIG. 10G shows the signal reconstruction error, which can be obtained by reconstructing the signal with the predicted parameter values, and comparing it with the noise-corrupted ground truth. To compute the error, the Rician log-likelihood $L_{lik}$ can be used. The log-likelihood can be normalized to its expectation value given the following exemplary prediction:

$$L_{lik}(M) = \frac{\sum_{i=1}^{Q} \log p(S_i | M_i)}{\sum_{i=1}^{Q} \int p(S_i | M_i) \log p(S_i | M_i) ds}, \quad (33)$$

where p(s|m) can be the Rician distribution with mean parameter m, M can be the prediction, S can be the measurement and the index i can refer to the q-space point. Values above unity can indicate that the model can be insufficient to describe the data, values below one can indicate over-fitting. The plots in FIG. 10G show the mean of $L_{lik}$ over the whole training set.

The overall error in parameters (e.g., see FIGS. 11A-11E) and signal (e.g., see FIG. 11F) can be functions of the number of features as defined by $l_{max}$=0, 2, 4, 5, 6 (elements 1105, 1110, 1120, 1125 and 1115, respectively), and the polynomial order, W, Eq. (32), which can be used for finding the Bayesian model, $\tilde{x}_B(f)$. The signal error can be defined in Eq. (33). The data can justify the choice $l_{max}$=2 and W=3.

Experiments with HCP Data.

The exemplary system, method and computer-accessible medium, was applied to data from a healthy subject provided by the Human Connectome Project ("HCP"), WU-Minn consortium. DWI data consists of 3×90 gradient directions at b-values 1, 2 and 3 ms/μm² and 18 non-diffusion weighted images with an isotropic voxel size of 1.25 mm, and was corrected for motion and EPI distortions. Polynomials of the order W=3 and $l_{max}$=2 were used. The SNR, or σ of the Rician distribution, was estimated from the standard deviation of the non-weighted b=0 images. FIG. 12A shows whole brain maps of the estimated parameters for the HCP dataset and their distributions within white matter (e.g., white matter masks obtained with SPM8 package).

Figure 13A:
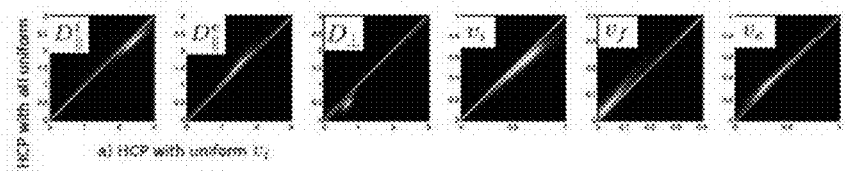
FIG. 13A-13C are exemplary maps showing the correlation between the microscopic parameters shown in FIG. 12A and those obtained using a modified training procedure according to an exemplary embodiment of the present disclosure.
Figure 13B:
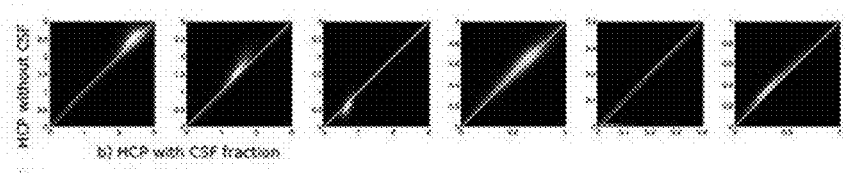
Figure 13C:
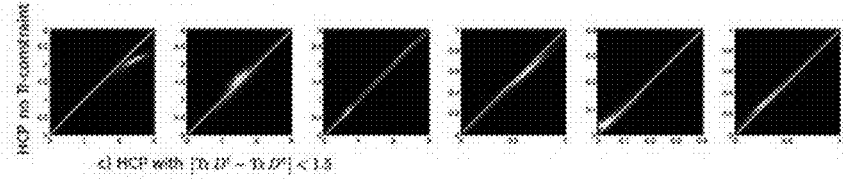

The choice of the prior distribution of volume fraction can have a minor effect on the microscopic parameters as illustrated in FIG. 13A for in-vivo HCP data. Models without the CSF compartment ($v_f$=0 in Eq. (27)) can yield slightly different parameters as illustrated in FIG. 13B for the HCP protocol. The correlation between microscopic parameters shown in FIG. 12B, and those obtained using modified training, can be evaluated. For example, as shown in the maps of FIG. 13A, the prior distribution of volume fractions can be changed from the uniform $v_i$ to the uniform on the plane $v_i+v_f+v_e=1$. The correlations in the maps of FIG. 13B can demonstrate the effect of excluding the CSF from the model ($v_f$=0). The limitation on the difference between traces of diffusion tensors inside and outside axons is shown in the maps shown in FIG. 13C. The volume fractions are less affected by the modifications.

To evaluate the fitting performance, the measurement and prediction by the normalized Rician log-likelihood were compared. Only white matter voxels with fractional anisotropy higher than 0.7 were considered to avoid any crossing areas where the simple dispersion model with a single main direction can be invalid. FIG. 12B shows a set of histograms of the distribution of the microscopic parameters within white matter. The markings include: the volume fraction inside axons (e.g., element 1225) and "free" water (CSF) fraction (e.g., element 1220). The narrow distribution of diffusivities, especially for $D_\parallel^e$ and $D_\perp$ (e.g., elements 1210 and 1205, respectively) can be interpreted in view of FIG. 10C as insufficient data was provided by this acquisition procedure.

FIG. 12C shows a graph of the distribution of the log-likelihood for the Poisson and Watson models (e.g., lines 1230 and 1235, respectively) and for the exemplary NODDI (e.g., line 1240).

NODDI can be a MLE based approach that can adopt a model similar to one defined in Eq. (27), and can be used here for comparison. For robustness and applicability to low quality data, NODDI can assume three constraints on the microstructure parameters. Both NODDI and the exemplary system, method and computer-accessible medium show a similar expected log-likelihood distribution. Although the corresponding signal courses can be very similar (see, e.g., graphs shown in FIG. 14), there can be differences in the parameters. FIG. 14 shows a single transversal slice of the estimated volume fraction $v_i$ together with a comparison with the intraaxonal fraction estimated by NODDI (note the difference of definitions). (See, e.g., Reference 8). The intra-axonal fraction $v_i=v_{ic}(1-v_{iso})$ and a map of fractional anisotropy ("FA") can be shown. There can be differences in the overall contrast, NODDI shows higher intraaxonal fractions in gray matter. In regions with threefold fiber crossing (e.g., arrow 1405 shown in FIG. 14) NODDI shows an artifact (the vertical stripe 1410), similar to the behavior of FA. Another difference can be found in the posterior part of the genu (highlighted by a circle 1415) where NODDI estimates a very low intraaxonal fraction. A very low restriction in this region seems not to be plausible, which suggests that the fitting of NODDI can be trapped in a local minimum.

FIGS. 15A-15C show the same image and graphs as those illustrated in FIGS. 12A-12C for the 2-shell60 protocol. The narrow distribution of diffusivities can be interpreted in view of FIG. 10E as insufficient data was provided by this acquisition procedure. As shown in the graphs of FIG. 15B, the diffusivities $D_\parallel^i$, $D_\parallel^e$ and $D_\perp$ are labeled as 1515, 1510 and 1505, respectively; the free CSF water fraction is 1520 and the intra-axonal water fraction is 1525. (See e.g., the graph shown in FIG. 15C).

Exemplary Experiments with 2-Shell Data.

The exemplary system, method and computer-accessible medium, according to an exemplary embodiment of the present disclosure, can be applied to a measurement of a healthy subject in a 3T scanner (e.g., Siemens TIM TRIO) using a 2-shell protocol with two shells at b-values 1 and 2 ms/μm² with 60 directions per shell, at an isotropic resolution of 2 mm, ⅝ partial Fourier, TR=10900 ms, TE=107 ms. The data was reconstructed with adaptive combine such that the noise distribution can be close to Rician. Additionally, Gibbs ringing artifacts were removed (See, e.g., Reference 27). The results can be quite similar to those obtained for the HCP data with the volume fractions in similar ranges. The data fitting quality of the model can be high as indicated by the distribution of $L_{lik}$ that has its peak around one, for example, which can be expected for a model without any systematic errors.

Exemplary Experiments with Hexagonal Data.

The exemplary system, method and computer-accessible medium, according to an exemplary embodiment of the present disclosure, can be applied to a measurement of a healthy subject in a 3T scanner (e.g., Siemens PRISMA) using a uniform filling of q-space. For the sake of rotation invariance, a hexagonal (e.g., cubic face-centered) distribution of q-space points inside a q-ball was used. Overall, 28 diffusion weighted images and two non-weighted images in 20 slices were measured at a resolution of 1×1×5 mm3 with ⅝ partial Fourier, TR=3100 ms, TE=84 ms. The overall acquisition time was below two minutes. Such a procedure can be applicable in acute stroke. The data was reconstructed with adaptive combine such that the noise distribution can be close to Rician. For the representation of the radial part of the signal kernel, simple 1, m-independent polynomial basis functions $R_k^{l,m}(b)=b^k$ with k=0, 1 can be used. This can result in three available features $f=\{f_0^1, f_0^2, f_2^1\}$, similar to the 2-shell60 protocol. The correlation statistics on the training set (see, e.g., FIGS. 10F and 10G) may only be slightly worse than what can be obtained with the 2shell-60 protocol despite four times smaller number of sampled q-space points. Within the exemplary system, method and computer-accessible medium this statistics can caution against trusting the diffusivity maps, which can be comparable in quality to those from the HCP protocol. (See, e.g., FIG. 16A). The narrow distributions of diffusivities can be centered around the mean values of the training set as it follows from the data shown in FIG. 10F. Measurements with improved SNR using three repetitions of the data (see, e.g., FIG. 16C) can only slightly improve the overall picture. As shown in the graphs of FIG. 16B, the diffusivities $D_\parallel^i$, $D_\parallel^e$ and $D_\perp$ are labeled as 1615, 1610 and 1605, respectively; the free CSF water fraction is 1620 and the intra-axonal water fraction is 1625. (See e.g., graph of FIG. 16C).

Figure 17:
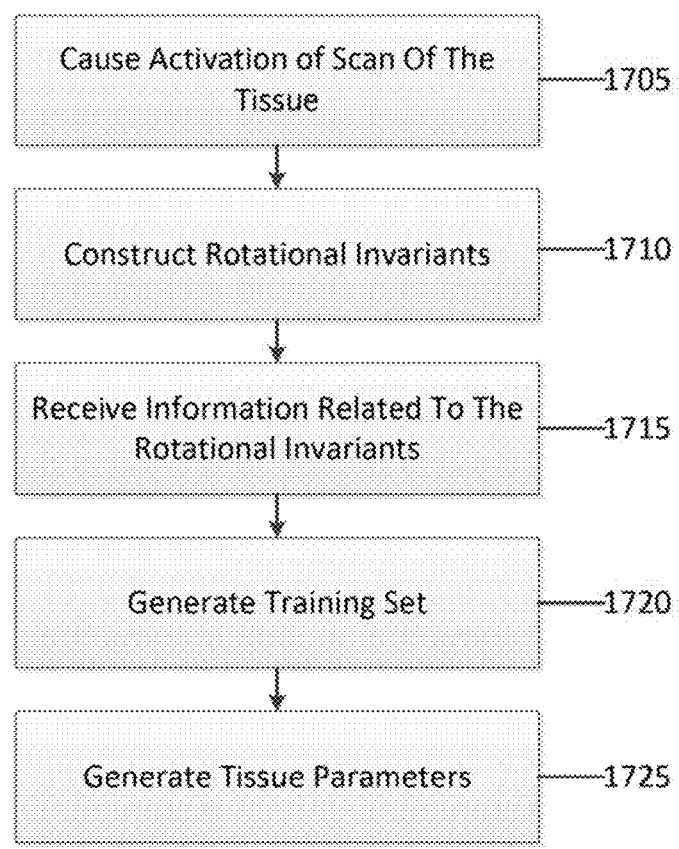
FIG. 17 is a flow diagram of an exemplary method for determining tissue parameters according to an exemplary embodiment of the present disclosure.

FIG. 17 shows a flow diagram of an exemplary method 1700 for determining tissue parameters according to an exemplary embodiment of the present disclosure. For example, at procedure 1705 a scan of the tissue can be activated, or caused to be activated. At procedure 1710, rotational invariants can be constructed based on the scan, and information related to the rotational invariants can be received at procedure 1715. At procedure 1720, a training set can be received and/or generated, which can be used to generate the tissue parameters at procedure 1725.

Figure 18:
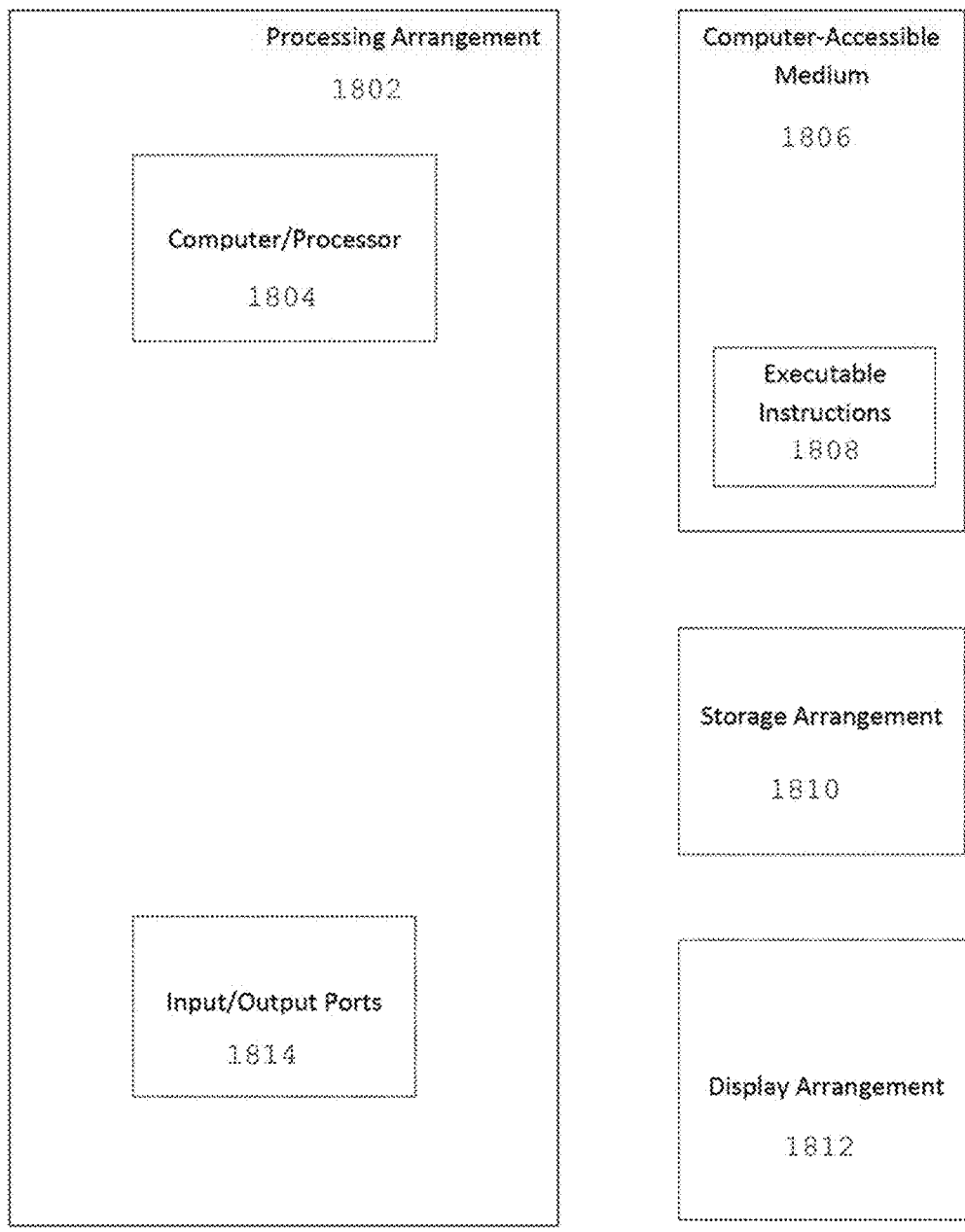
FIG. 18 is an illustration of an exemplary block diagram of an exemplary system in accordance with certain exemplary embodiments of the present disclosure.

As shown in FIG. 18, for example a computer-accessible medium 1806 (e.g., as described herein above, a storage device such as a hard disk, floppy disk, memory stick, CD-ROM, RAM, ROM, etc., or a collection thereof) can be provided (e.g., in communication with the processing arrangement 1802). The computer-accessible medium 1806 can contain executable instructions 1808 thereon. In addition or alternatively, a storage arrangement 1810 can be provided separately from the computer-accessible medium 1806, which can provide the instructions to the processing arrangement 1802 so as to configure the processing arrangement to execute certain exemplary procedures, processes and methods, as described herein above, for example.

Further, the exemplary processing arrangement 1802 can be provided with or include an input/output arrangement 1814, which can include, for example a wired network, a wireless network, the internet, an intranet, a data collection probe, a sensor, etc. As shown in FIG. 18, the exemplary processing arrangement 1802 can be in communication with an exemplary display arrangement 1812, which, according to certain exemplary embodiments of the present disclosure, can be a touch-screen configured for inputting information to the processing arrangement in addition to outputting information from the processing arrangement, for example. Further, the exemplary display 1812 and/or a storage arrangement 1810 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
[1] T E J Behrens, M W Woolrich, M Jenkinson, H Johansen-Berg, R G Nunes, S Clare, P M Matthews, J M Brady, and S M Smith, "Characterization and propagation of uncertainty in diffusion-weighted MR imaging," Magn Reson Med 50, 1077-88 (2003).
[2] Christopher D Kroenke, Joseph J H Ackerman, and Dmitriy A Yablonskiy, "On the nature of the NAA diffusion attenuated MR signal in the central nervous system," Magn Reson Med 52, 1052-9 (2004).
[3] Sune N. Jespersen, Christopher D. Kroenke, Leif Ostergaard, Joseph J. H. Ackerman, and Dmitriy A. Yablonskiy, "Modeling dendrite density from magnetic resonance diffusion measurements," Neuroimage 34, 1473-1486 (2007).
[4] Sune N. Jespersen, Carsten R. Bjarkam, Jens R. Nyengaard, M. Mallar Chakravarty, Brian Hansen, Thomas Vosegaard, LeifOstergaard, Dmitriy Yablonskiy, Niels Chr. Nielsen, and Peter Vestergaard-Poulsen, "Neurite density from magnetic resonance diffusion measurements at ultrahigh field: Comparison with light microscopy and electron microscopy," Neuroimage 49, 205-216 (2010).
[5] Y Assaf, R Z Freidlin, G K Rohde, and P J Basser, "New modeling and experimental framework to characterize hindered and restricted water diffusion in brain white matter," Magnetic Resonance In Medicine 52, 965-978 (2004).
[6] Els Fieremans, Dmitry S. Novikov, Jens H. Jensen, and Joseph A. Helpern, "Monte Carlo study of a two-compartment exchange model of diffusion," NMR in Biomedicine 23, 711-724 (2010).

[7] Els Fieremans, Jens H Jensen, and Joseph A Helpern, "White matter characterization with diffusional kurtosis imaging," Neuroimage 58, 177-88 (2011).
[8] Hui Zhang, Torben Schneider, Claudia A Wheeler-Kingshott, and Daniel C Alexander, "NODDI: practical in vivo neurite orientation dispersion and density imaging of the human brain," Neuroimage 61, 1000-16 (2012).
[9] Dmitry S Novikov, Jens H Jensen, Joseph A Helpern, and Els Fieremans, "Revealing mesoscopic structural universality with diffusion," Proc Natl Acad Sci USA 111, 5088-93 (2014).
[10] Els Fieremans, Lauren M Burcaw, Hong-Hsi Lee, Gregory Lemberskiy, Jelle Veraart, and Dmitry S Novikov, "In vivo observation and biophysical interpretation of time-dependent diffusion in human white matter," NeuroImage (2016).
[11] Els Fieremans, Jens H. Jensen, Joseph A. Helpern, Sungheon Kim, Robert I. Grossman, Matilde Inglese, and Dmitry S. Novikov, "Diffusion distinguishes between axonal loss and demyelination in brain white matter," Proceedings of the International Society of Magnetic Resonance in Medicine 20, p. 714 (2012).
[12] Lauren M Burcaw, Els Fieremans, and Dmitry S Novikov, "Mesoscopic structure of neuronal tracts from time-dependent diffusion," NeuroImage 114, 18-37 (2015).
[13] Dmitry S. Novikov and Els Fieremans, "Relating extracellular diffusivity to cell size distribution and packing density as applied to white matter," Proceedings of the International Society of Magnetic Resonance in Medicine 20, p. 1829 (2012).
[14] Maira Tariq, Torben Schneider, Daniel C Alexander, Claudia A Gandini Wheeler-Kingshott, and Hui Zhang, "Bingham-noddi: Mapping anisotropic orientation dispersion of neurites using diffusion mri," NeuroImage (2016).
[15] Ileana O Jelescu, Jelle Veraart, Els Fieremans, and Dmitry S Novikov, "Degeneracy in model parameter estimation for multi-compartmental diffusion in neuronal tissue," NMR in Biomedicine 29, 33-47 (2016).
[16] Jens H Jensen, G Russell Glenn, and Joseph A Helpern, "Fiber ball imaging," NeuroImage 124, 824-833 (2016).
[17] Enrico Kaden, Frithjof Kruggel, and Daniel C Alexander, "Quantitative mapping of the per-axon diffusion coefficients in brain white matter," Magnetic resonance in medicine (2015).
[18] Jens H Jensen, Joseph A Helpern, Anita Ramani, Hanzhang Lu, and Kyle Kaczynski, "Diffusional kurtosis imaging: the quantification of non-gaussian water diffusion by means of magnetic resonance imaging," Magn Reson Med 53, 1432-40 (2005).
[19] Bibek Dhital, Elias Kellner, Marco Reisert, and Valerij G Kiselev, "Isotropic diffusion weighting provides insight on diffusion compartments in human brain white matter in vivo," Proceedings of the International Society of Magnetic Resonance in Medicine 23, p. 2788. (2015).
[20] Filip Szczepankiewicz, Samo Lasivc, Danielle van Westen, Pia C Sundgren, Elisabet Englund, Carl-Fredrik Westin, Freddy Strahlberg, Jimmy Litt, Daniel Topgaard, and Markus Nilsson, "Quantification of microscopic diffusion anisotropy disentangles effects of orientation dispersion from microstructure: applications in healthy volunteers and in brain tumors," NeuroImage 104, 241-252 (2015).
[21] Marco Reisert, Valerij G Kiselev, Bibek Dihtal, Elias Kellner, and DS Novikov, "Mesoft: unifying diffusion modelling and fiber tracking," in *Medical Image Computing and Computer-Assisted Intervention—MICCA 2014* (Springer, 2014) pp. 201-208.
[22] Jelle Veraart, Jeny Rajan, Ronald R Peeters, Alexander Leemans, Stefan Sunaert, and Jan Sijbers, "Comprehensive framework for accurate diffusion mri parameter estimation," Magn Reson Med 70, 972-84 (2013).
[23] Kip S Thorne, "Multipole expansions of gravitational radiation," Reviews of Modern Physics 52, 299-339 (1980).
[24] Valerij G Kiselev, "Diffusion MRI: Theory, methods and applications," (Ed. Jones, D. K., Oxford University Press, New York, 2010) Chap. 10. The cumulant expansion: An overarching mathematical framework for understanding diffusion NMR.
[25] Jelle Veraart, Els Fieremans, and Dmitry S Novikov, "Diffusion MRI noise mapping using random matrix theory," Magnetic resonance in medicine DOI: 10.1002/mrm.26059 (2016).
[26] Cheng Guan Koay and Peter J Basser, "Analytically exact correction scheme for signal extraction from noisy magnitude MR signals," Journal of Magnetic Resonance 179, 317-322 (2006).
[27] Elias Kellner, Bibek Dhital, Valerij G Kiselev, and Marco Reisert, "Gibbs-ringing artifact removal based on local subvoxel-shifts," Magnetic resonance in medicine DOI: 10.1002/mrm.26054 (2015).
[28] Jelle Veraart, Els Fieremans, Ileana O Jelescu, Florian Knoll, and Dmitry S Novikov, "Gibbs ringing in diffusion MRI," Magnetic resonance in medicine DOI: 10.1002/mrm.25866 (2015).
[29] Stephen M Smith, Mark Jenkinson, Mark W Woolrich, Christian F Beckmann, Timothy E J Behrens, Heidi Johansen-Berg, Peter R Bannister, Marilena De Luca, Ivana Drobnjak, David E Flitney, et al., "Advances in functional and structural MR image analysis and implementation as FSL," Neuroimage 23, S208-S219 (2004).
[30] International Patent Application No. PCT US2014/033189
[31] U.S. Provisional Patent Application No. 62/162,164

What is claimed is:

1. A non-transitory computer-accessible medium having stored thereon computer-executable instructions for determining a plurality of tissue parameters of at least one tissue, wherein, when a computer arrangement executes the instructions, the computer arrangement is configured to perform procedures comprising:
receiving information related to a set of rotational invariants related to the tissue parameters that are contained within at least one diffusion magnetic resonance (dMR) image of the at least one tissue;
generating the tissue parameters using (i) the set of rotational invariants based on the information, and (ii) at least one non-linear fitting procedure applied to each voxel of an image of at the least one tissue, wherein the generation of the tissue parameters using the generating procedure is performed by factorizing a response of individual fiber segments of the at least one tissue from an orientation distribution function (ODF) based on the set of rotational invariants; and
constructing the orientation distribution function using an exact factorization relation.

2. The computer-accessible medium of claim 1, wherein the computer arrangement is further configured to determine a plurality of tensor tissue parameters based on a plurality of scalar tissue parameters and a plurality of diffusion moments.

3. The computer-accessible medium of claim 2, wherein:
the scalar tissue parameters include at least one of (i) a diffusivity inside neurites of the at least one tissue, (ii) the diffusivities outside the neurites, or (iii) a neurite water fraction of the at least one tissue; and
the tensor tissue parameters include an orientation distribution function of the at least one tissue.

4. The computer-accessible medium of claim 2, wherein a number of the tissue parameters are based on a maximum order of the diffusion moments.

5. The computer-accessible medium of claim 1, wherein the computer arrangement is further configured to cause an activation of a magnetic resonance imaging apparatus to acquire the dMR image.

6. The computer-accessible medium of claim 1, wherein diffusion rotational invariants include diffusion moments and wherein the computer arrangement is configured to factorize the response of the individual fiber segments using at least one scalar tensor factorization of the diffusion moments, and relations between the tissue parameters and the rotational invariants that are based on the diffusion moments.

7. The computer-accessible medium of claim 1, wherein the set of rotational invariants are of a rotation group SO(3).

8. The computer-accessible medium of claim 1, wherein the computer arrangement is further configured to estimate the information using a plurality of cumulant tensors.

9. The computer-accessible medium of claim 8, wherein the tissue parameters include at least two branches of tissue parameters, and wherein the computer arrangement is further configured to select one of the branches based on prior information about a range of model parameters values.

10. The computer-accessible medium of claim 1, wherein the computer arrangement is configured to generate the tissue parameters using at least one minimization function with respect to a plurality of model parameters.

11. The computer-accessible medium of claim 1, wherein the diffusion rotational invariants include diffusion moments, and wherein the computer arrangement is configured to factorize the response of the individual fiber segments using at least one scalar-tensor factorization of the diffusion moments, and relations between the tissue parameters and the rotational invariants that are based on the diffusion moments.

12. The computer-accessible medium of claim 11, wherein the computer arrangement is further configured to initialize the at least one non-linear fitting procedure based on the tissue parameters.

13. The computer-accessible medium of claim 1, wherein the at least one non-linear fitting procedure is based on a prevalence procedure.

14. The computer-accessible medium of claim 13, wherein the prevalence procedure includes (i) beginning at a number of random initializations, (ii) clustering outcomes of the prevalence procedure, and (iii) and selecting a largest cluster.

15. The computer-accessible medium of claim 1, wherein the computer arrangement is further configured to initialize the at least one non-linear fitting procedure using fit outcomes related by a duality transformation.

16. The computer-accessible medium of claim 1, wherein the computer arrangement is further configured to determine a plurality of tensor tissue parameters based on scalar tissue parameters and the rotational invariants.

17. The computer-accessible medium of claim 1, wherein the computer arrangement is further configured to receive at least one signal related to the at least one dMR image.

18. The computer-accessible medium of claim 17, wherein the computer arrangement is further configured to construct the rotational invariants based on the at least one dMR signal.

19. The computer-accessible medium of claim 18, wherein the computer arrangement is further configured to:
generate at least one training set; and
generate the tissue parameters based on the at least one training set.

20. The computer-accessible medium of claim 19, wherein the computer arrangement is further configured to generate the tissue parameters using at least one further non-linear fitting procedure.

21. The computer-accessible medium of claim 20, wherein the computer arrangement is further configure to initialize the at least one further non-linear fitting procedure based on the tissue parameters using the at least one training set.

22. A system for determining a plurality of tissue parameters of at least one tissue, comprising:
a computer hardware arrangement configured to:
receive information related to a set of rotational invariants related to the tissue parameters that are contained within at least one diffusion magnetic resonance (dMR) image of the at least one tissue;
generate the tissue parameters using (i) the set of rotational invariants based on the information, and (ii) at least one non linear fitting procedure applied to each voxel of an image of at the least one tissue, wherein the generation of the tissue parameters using the generating procedure is performed by factorizing a response of individual fiber segments of the at least one tissue from an orientation distribution function (ODF) based on the set of rotational invariants; and
construct the orientation distribution function using an exact factorization relation.

23. A method for determining a plurality of tissue parameters of at least one tissue, comprising:
receiving information related to a set of rotational invariants related to the tissue parameters that are contained within at least one diffusion magnetic resonance (dMR) image of the at least one tissue;
with a computer hardware arrangement, generating the tissue parameters using (i) the set of rotational invariants based on the information, and (ii) at least one non-linear fitting procedure applied to each voxel of an image of at the least one tissue, wherein the generation of the tissue parameters is performed by factorizing a response of individual fiber segments of the at least one tissue from an orientation distribution function (ODF) based on the set of rotational invariants; and
constructing the orientation distribution function using an exact factorization relation.

24. A non-transitory computer-accessible medium having stored thereon computer executable instructions for determining a plurality of tissue parameters of at least one tissue, wherein, when a computer arrangement executes the instructions, the computer arrangement is configured to perform procedures comprising:
receiving information related to a plurality of diffusion rotational invariants contained within at least one diffusion magnetic resonance (dMR) image of the at least one tissue;
generating the tissue parameters using (i) a set of rotational invariants related to the tissue parameters based on the information, and (ii) at least one non-linear fitting procedure applied to each voxel of an image of at the least one tissue; and determining a plurality of tensor tissue parameters based on a plurality of scalar tissue parameters and a plurality of diffusion moments, wherein the scalar tissue parameters include at least one of (i) a diffusivity inside neurites of the at least one tissue, (ii) the diffusivities outside the neurites, or (iii) a neurite water fraction of the at least one tissue, and wherein the tensor tissue parameters include an orientation distribution function of the at least one tissue.

25. The computer-accessible medium of claim 24, wherein the diffusion rotational invariants include the diffusion moments, and wherein the computer arrangement is further configured to factorize a response of individual fiber segments using at least one scalar tensor factorization of the diffusion moments and relations between the tissue parameters and the rotational invariants that are based on the diffusion moments.

26. A system for determining a plurality of tissue parameters of at least one tissue, comprising:

a computer hardware arrangement configured to:
receive information related to a plurality of diffusion rotational invariants contained within at least one diffusion magnetic resonance (dMR) image of the at least one tissue;
generate the tissue parameters using (i) a set of rotational invariants related to the tissue parameters based on the information, and (ii) at least one non-linear fitting procedure applied to each voxel of an image of at the least one tissue; and
determine a plurality of tensor tissue parameters based on a plurality of scalar tissue parameters and a plurality of diffusion moments,
wherein the scalar tissue parameters include at least one of (i) a diffusivity inside neurites of the at least one tissue, (ii) the diffusivities outside the neurites, or (iii) a neurite water fraction of the at least one tissue, and
wherein the tensor tissue parameters include an orientation distribution function of the at least one tissue.

27. The system of claim 26, wherein the diffusion rotational invariants include the diffusion moments, and wherein the computer hardware arrangement is further configured to factorize a response of individual fiber segments using at least one scalar tensor factorization of the diffusion moments and relations between the tissue parameters and the rotational invariants that are based on the diffusion moments.

28. A method for determining a plurality of tissue parameters of at least one tissue, comprising:

receiving information related to a plurality of diffusion rotational invariants contained within at least one diffusion magnetic resonance (dMR) image of the at least one tissue;
generating the tissue parameters using (i) a set of rotational invariants related to the tissue parameters based on the information, and (ii) at least one non-linear fitting procedure applied to each voxel of an image of at the least one tissue; and
using a computer hardware arrangement, determining a plurality of tensor tissue parameters based on a plurality of scalar tissue parameters and a plurality of diffusion moments,
wherein the scalar tissue parameters include at least one of (i) a diffusivity inside neurites of the at least one tissue, (ii) the diffusivities outside the neurites, or (iii) a neurite water fraction of the at least one tissue, and
wherein the tensor tissue parameters include an orientation distribution function of the at least one tissue.

29. The method of claim 28, wherein the diffusion rotational invariants include the diffusion moments, and further comprising factorizing a response of individual fiber segments using at least one scalar tensor factorization of the diffusion moments and relations between the tissue parameters and the rotational invariants that are based on the diffusion moments.

* * * * *

UNITED STATES PATENT AND TRADEMARK OFFICE
CERTIFICATE OF CORRECTION

PATENT NO. : 10,360,472 B2
APPLICATION NO. : 15/156250
DATED : July 23, 2019
INVENTOR(S) : Novikov et al.

Page 1 of 1

It is certified that error appears in the above-identified patent and that said Letters Patent is hereby corrected as shown below:

In the Specification

Please amend the second paragraph under Column 1, Lines 16-21 with the following paragraph as follows:
STATEMENT REGARDING FEDERALLY SPONSORED RESEARCH
This invention was made with government support under grant number R01 NS088040 awarded by the National Institutes of Health. The government has certain rights in this invention.

Signed and Sealed this
Seventeenth Day of March, 2020

Andrei Iancu
*Director of the United States Patent and Trademark Office*